(12) United States Patent
Bennett et al.

(10) Patent No.: US 7,119,114 B1
(45) Date of Patent: *Oct. 10, 2006

(54) PYRAZOLOANTHRONE AND DERIVATIVES THEREOF AS JNK INHIBITORS AND COMPOSITIONS AND METHODS RELATED THERETO

(75) Inventors: Brydon L. Bennett, San Diego, CA (US); Shripad S. Bhagwat, San Diego, CA (US); Anthony M. Manning, San Diego, CA (US); Brion W. Murray, San Diego, CA (US); Eoin C. O'Leary, San Diego, CA (US); Yoshitaka Satoh, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/642,557

(22) Filed: Aug. 18, 2000

Related U.S. Application Data

(60) Provisional application No. 60/240,928, filed on Aug. 19, 1999.

(51) Int. Cl.
*A61K 31/416* (2006.01)
*C07D 231/54* (2006.01)

(52) U.S. Cl. .................. 514/403; 514/406; 548/358.5; 548/357.1

(58) Field of Classification Search ................ 514/406, 514/403; 548/358.5, 356.5, 357.1
See application file for complete search history.

(56) References Cited

U.S. PATENT DOCUMENTS

| | | | |
|---|---|---|---|
| 4,198,518 A | | 4/1980 | Tzikas |
| 4,202,827 A | * | 5/1980 | Tzikas .................... 552/238 |
| 4,556,654 A | * | 12/1985 | Showalter et al. ....... 514/228.2 |
| 6,162,613 A | | 12/2000 | Su et al. |

FOREIGN PATENT DOCUMENTS

| | | |
|---|---|---|
| CS | 146895 | 2/1972 |
| DE | 1257149 | * 12/1967 |
| EP | 0 208 211 | 1/1987 |
| GB | 1293557 | 9/1970 |
| GB | 1404969 | 8/1973 |
| GB | 1576217 | 7/1977 |
| WO | WO 99/53927 | 10/1999 |
| WO | WO 00/35909 | 6/2000 |
| WO | WO 01/12609 | 2/2001 |
| WO | WO 01/12621 A1 | 2/2001 |
| WO | WO 02/085396 | 10/2002 |

OTHER PUBLICATIONS

STN International® CAPLUS Database, Accession No. 1997:491798; Ivanova et al., Poverkhnost (1997), (4-5), 193-201.*
STN International® CAPLUS Database, Accession No. 1994:30709, Sokolyuk et al., Zh. Org. Khim. (1992), 28(10), 2193-200.*
STN International® CAPLUS Database, Accession No. 1973:406796, Arient, Patent No. CS146895 (1973).*
STN International® CAPLUS Database, Accession No. 1989:185177, Showalter et al. (1988).*
Laakso et al., CA 51:76969, 1957.*
Mosby et al., CA 54:80551, 1960.*
Akamatsu, CA 58:27252, 1963.*
Ames et al., 1987, "An integrated concept of amebicidal action: electron transfer and oxy radicals", Free Radical Biol. Med. 3:85-96.
Aspenström et al., 1996, "Two GTPases, Cdc42 and Rac, bind directly to a protein implicated in the immunodeficiency disorder Wiskott-Aldrich syndrome", Curr. Biol. 6:70-75.
Chen et al., 1996, "Activation and inhibition of the AP-1 complex in human breast cancer cells", Mol. Carcinogenesis 15:215-226.
Dong et al., 1998, "Defective T cell differentiation in the absence of Jnk1", Science 282:2092-2095.
Faris et al., 1996, "Regulation of interleukin-2 transcription by inducible stabile expression of dominant negative and dominant active mitogen-activated protein kinase kinase kinase in Jurkat T cells", J. Biol. Chem. 271:27366-27373.
Galushko and Dokunikhin, 1977, "Pyrazoloanthrone derivatives I. Reactivity of 3-aminopyrazoloanthrone", Khimiya Geterotsiklicheskikh Soedinenii, 7:956-961.

(Continued)

*Primary Examiner*—Laura L. Stockton
(74) *Attorney, Agent, or Firm*—Jones Day

(57) ABSTRACT

Compounds having activity as selective inhibitors of JNK are disclosed The compounds of this invention are pyrazoloanthrone and derivatives thereof having the following structure:

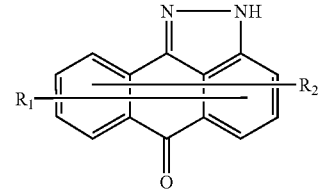

wherein $R_1$ and $R_2$ are as defined herein. Such compounds have utility in the treatment of a wide range of conditions that are responsive to JNK inhibition. Thus, methods of treating such conditions are also disclosed, as are pharmaceutical compositions containing one or more compounds of the above compounds.

19 Claims, 7 Drawing Sheets

OTHER PUBLICATIONS

Gum et al., 1997, "Regulation of 92 kDa type IV collagenase expression by the jun aminoterminal kinase- and the extracellular signal-regulated kinase- dependent signaling cascades", Oncogene 14:1481-1493.

Gvon et al., 1994, "Amino-imino tautomerism and intramolecular cyclization of 4, 9-diamino-1, 10-anthraquinone-1-tosylimines" Dokl. Akad. Nauk, 334:465-468 (in Russian with English abstract).

Han et al., 1999, "Jun N-terminal kinase in rheumatoid arthritis", J. Pharmacol. Exp. Therap. 291:124-130.

Hartley et al., 1988, "Characteristics of the interaction of anthrapyrazole anticancer agents with deoxyribonucleic acids: structural requirements for DNA binding, intercalation, and photosensitization", Mol. Pharmacol. 33:265-271.

Hibi et al., 1993, "Identification of an oncoprotein- and UV-responsive protein kinase that binds and potentiates the c-Jun activation domain", Genes Dev. 7:2135-2148.

Ishizuka et al., 1997, "Mast cell tumor necrosis factor α production is regulated by MEK kinases", Proc. Natl. Acad. Sci. USA 94:6358-6363.

Ivanova et al., 1997, "XPS investigation of electronic structure of pyrazolanthrone and its derivatives" Poverkhnost, 4-5:193-201.

Judson, 1992, "The anthrapyrazoles: a new class of compounds with clinical activity in breast cancer", Semin. Oncol. 19:687-694.

Karin et al., 1997, "AP-1 function and regulation", Curr. Opin. Cell. Biol. U9:240-246.

Lange-Carter et al., 1993, "A divergence in the MAP kinase regulatory network defined by MEK kinase and Raf", Science 260:315-319.

Li et al., 1996, "Blocked signal transduction to the ERK and JNK protein kinases in anergic CD4$^+$ T cells", Science 271:1272-1276.

Li et al., 1996, "The Ras-JNK pathway is involved in shear-induced gene expression", Mol. Cell. Biol. 16:5947-5954.

Lin et al., 1995, "Identification of a dual specificity kinase that activates the Jun kinases and p38-Mpk2", Science 268:286-290.

Manning and Mercurio, 1997, "Transcription inhibitors in inflammation", Exp. Opin. Invest. Drugs 6:555-567.

Milne et al., 1995, "p53 is phosphorylated *in vitro* and *in vivo* by an ultraviolet radiation-induced protein kinase characteristic of the c-Jun kinase, JNK1", J. Biol. Chem. 270:5511-5518.

Mohit et al., 1995, "p49$^{3F12}$ kinase: a novel MAP kinase expressed in a subset of neurons in the human nervous system", Neuron 14:67-78.

Nishina et al., 1997, "Imparied CD28-mediated interleukin 2 production and proliferation in stress kinase SAPK/ERK1 kinase (SEK1)/mitogen-activated protein kinase kinase 4 (MKK4)-deficient T lymphocytes", J. Exp. Med. 186:941-953.

Okamoto et al., 1997, "Selective activation of the JNK/AP-1 pathway in Fas-mediated apoptosis of rheumatoid arthritis synoviocytes", Arthritis & Rheumatism 40:919-926.

Pombo et al., 1994, "The stress-activated protein kinases are major c-Jun amino-terminal kinases activated by ischemia and reperfusion", J. Biol. Chem. 269:26546-26551.

Raitano et al., 1995, "The Bcr-Abl leukemia oncogene activates Jun kinase and requires Jun for transformation", Proc. Natl. Acad. Sci. USA 92:11746-11750.

Sabapathy et al., 1999, "JNK2 is required for efficient T-cell activation and apoptosis but not for normal lymphocyte development", Curr. Biol. 9:116-125.

Showalter et al., 1987, "Anthrapyrazole anticancer agents. Synthesis and structure-activity relationships against murine leukemias", J. Med. Chem. 30:121-131.

Showalter et al., 1984, "5-[(Aminoalkyl)amino]-substituted anthral[1,9-cd]pyrazol-6(2H)-ones as novel anticancer agents. Synthesis and biological evaluation", J. Med. Chem. 27:253-255.

Singh and Shah, 1978, "Reactions of 2,2'-ethylene-bis-anthrapyrazolone", Indian J. -Chem. 16B:100-102.

Sokolyuk et al., 1992, "Synthesis and photochemical properties of peri-phenoxy derivatives of 6H-anthra[1,9-cd]-6-pyrazolone (pyrazolanthrone)", Zhurnal Organicheskoi Khimii 28:2193-200.

Su et al., 1994, "JNK is involved in signal integration during costimulation of T lymphocytes", Cell 77:727-736.

Swantek et al., 1997, "Jun N-terminal kinase/stress-activated protein kinase (JNK/SAPK) is required for lipopolysaccharide stimulation of tumor necrosis factor alpha (TNF-α) translation: glucocorticoids inhibit TNF-α translation by blocking JNK/SAPK", Mol. Cell. Biol. 17:6274-6282.

Szabo et al., 1996, "Altered cJUN expression: an early event in human lung carcinogenesis", Cancer Res. 56:305-315.

Tournier et al., 1997, "Mitogen-activated protein kinase kinase 7 is an activator of the c-Jun $NH_2$-terminal kinase", Proc. Natl. Acad. Sci. USA 94:7337-7342.

Whitmarsh and Davis, 1996, "Transcription factor AP-1 regulation by mitogen-activated protein kinase signal transduction pathways", Mol. Med. 74:589-607.

Yan et al., 1994, "Activation of stress-activated protein kinase by MEKK1 phosphorylation of its activator SEK1", Nature 372:798-800.

Yang et al., 1998, "Differentiation of CD4$^+$ T cells to Th1 cells requires MAP kinase JNK2", Immunity 9:575-585.

Yin et al., 1997, "Tissue-specific pattern of stress kinase activation in ischemic/reperfused heart and kidney", J. Biol. Chem. 272:19943-19950.

CAS No. 130:153598d for Gwon et al., "Direct amination of 6H-anthra(9, 1-cd)isothiazol-6-one 2,2-dioxides", Dokl. Akad. Nauk, 359:357-61, 1998.

CAS No. 102:205411f for Mitsubishi Chemical Industries Co., Ltd., JP 60 028,454.

CAS No. 104:208328m for Mitsubishi Chemical Industries Co., Ltd., JP 60 250,052.

CAS No. 103:143360y for Mitsubishi Chemical Industries Co., Ltd., JP 60 092,355.

Web page printout of Dec. 18, 2002 for http://www.calbiochem.com/Products/ProductDetail_CBCB.asp?catNO=420119 (cat. No. 420119).

Spiegelman et al., "Regulation of Adipocyte Gene Expression in Differentiation and Syndromes of Obesity/Diabetes", *J. of Biol. Chem.* 268:6823-6826 (1993).

Hirosumi et al., "A central role for JNK in obesity and insulin resistance", *Letters to Nature* 420:333-336 (2002).

Showalter et al, "Design, Tumor Biology, and Biochemical Pharmacology of Anthrapyrazoles" *Bioact. Mol. Chapter VI*:201-243 (1988).

CAS No. 86:121031v for Shah et al., "Thiocyanation of 1-aminoanthraquinones", Indian J. Chem. 14B:625-626, 1976.

CAS No. 102:205411f for Mitsubishi Chemical Industries Co., Ltd., JP 60 028,454, 1985.

CAS No. 140:208328m for Mitsubishi Chemical Industries Co., Ltd., JP 60 250,052, 1986.

CAS No. 103:143360y for Mitsubishi Chemical Industries Co., Ltd., JP 60 092:355, 1985.

\* cited by examiner

PYRAZOLOANTHRONE AND DERIVATIVES THEREOF AS JNK INHIBITORS AND COMPOSITIONS AND METHODS RELATED THERETO

CROSS-REFERENCE TO RELATED APPLICATION

This application claims the benefit of U.S. Provisional Application No. 60/240,928 filed Aug. 19, 1999 (incorporated by reference in its entirety).

TECHNICAL FIELD

This invention is generally directed to pyrazoloanthrone and derivatives thereof which have utility over a wide range of indications, including activity as Jun N-terminal kinase inhibitors, and related compositions and methods.

BACKGROUND OF THE INVENTION

The Jun N-terminal kinase (JNK) pathway is activated by exposure of cells to environmental stress or by treatment of cells with pro-inflammatory cytokines. Targets of the JNK pathway include the transcription factors c-jun and ATF2 (Whitmarsh A. J., and Davis R. J. *J. Mol. Med.* 74:589–607, 1996). These transcription factors are members of the basic leucine zipper (bZIP) group that bind as homo- and heterodimeric complexes to AP-1 and AP-1-like sites in the promoters of many genes (Karin M., Liu Z. G. and Zandi E. *Curr Opin Cell Biol* 9:240–246, 1997). JNK binds to the N-terminal region of c-jun and ATF-2 and phosphorylates two sites within the activation domain of each transcription factor (Hibi M., Lin A., Smeal T., Minden A., Karin M. *Genes Dev.* 7:2135–2148, 1993; Mohit A. A., Martin M. H., and Miller C. A. *Neuron* 14:67–75, 199)]. Three JNK enzymes have been identified as products of distinct genes (Hibi et al, supra; Mohit et al., supra). Ten different isoforms of JNK have been identified. These represent alternatively spliced forms of three different genes: JNK1, JNK2 and JNK3. JNK1 and 2 are ubiquitously expressed in human tissues, whereas JNK3 is selectively expressed in the brain, heart and testis (Dong, C., Yang, D., Wysk, M., Whitmarsh, A., Davis, R., Flavell, R. *Science* 270:1–4, 1998). Gene transcripts are alternatively spliced to produce four-JNK1 isoforms, four-JNK2 isoforms and two-JNK3 isoforms. JNK1 and 2 are expressed widely in mammalian tissues, whereas JNK3 is expressed almost exclusively in the brain. Selectivity of JNK signaling is achieved via specific interactions of JNK pathway components and by use of scaffold proteins that selectively bind multiple components of the signaling cascade. JIP-1 (JNK-interacting protein-1) selectively binds the MAPK module, MLK→JNKK1→JNK.12, 13 It has no binding affinity for a variety of other MAPK cascade enzymes. Different scaffold proteins are likely to exist for other MAPK signaling cascades to preserve substrate specificity.

JNKs are activated by dual phosphorylation on Thr-183 and Tyr-185. JNKK1 (also known as MKK 4) and JNKK2 (MKK7), two MAPKK level enzymes, can mediate JNK activation in cells (Lin A., Minden A., Martinetto H., Claret F.-Z., Lange-Carter C., Mercurio F., Johnson G. L., and Karin M. *Science* 268:286–289, 1995; Tournier C., Whitmarsh A. J., Cavanagh J., Barrett T., and Davis R. J. *Proc. Nat. Acad. Sci. USA* 94:7337–7342, 1997). JNKK2 specifically phosphorylates JNK, whereas JNKK1 can also phosphorylate and activate p38. Both JNKK1 and JNKK2 are widely expressed in mammalian tissues. JNKK1 and JNKK2 are activated by the MAPKKK enzymes, MEKK1 and 2 (Lange-Carter C. A., Pleiman C. M., Gardner A. M., Blumer K. J., and Johnson G. L. *Science* 260:315–319, 1993; Yan M., Dai J. C., Deak J. C., Kyriakis J. M., Zon L. I., Woodgett J. R., and Templeton D. J. *Nature* 372:798–781, 1994). Both MEKK1 and MEKK2 are widely expressed in mammalian tissues.

Activation of the JNK pathway has been documented in a number of disease settings, providing the rationale for targeting this pathway for drug discovery. In addition, molecular genetic approaches have validated the pathogenic role of this pathway in several diseases. For example, autoimmune and inflammatory diseases arise from the over-activation of the immune system. Activated immune cells express many genes encoding inflammatory molecules, including cytokines, growth factors, cell surface receptors, cell adhesion molecules and degradative enzymes. Many of these genes are regulated by the JNK pathway, through activation of the transcription factors AP-1 and ATF-2, including TNFa, IL-2, E-selectin and matrix metalloproteinases such as collagenase-1 (Manning A. M. and Mercurio F. *Exp Opin Invest Drugs* 6: 555–567, 1997). Monocytes, tissue macrophages and tissue mast cells are key sources of TNFa production. The JNK pathway regulates TNFa production in bacterial lipopolysaccharide-stimulated macrophages, and in mast cells stimulated through the FceRII receptor (Swantek J. L., Cobb M. H., Geppert T. D. *Mol. Cell. Biol.* 17:6274–6282, 1997; Ishizuka, T., Tereda N., Gerwins, P., Hamelmann E., Oshiba A., Fanger G. R., Johnson G. L., and Gelfland E. W. *Proc. Nat. Acad. Sci. USA* 94:6358–6363, 1997). Inhibition of JNK activation effectively modulates TNFa secretion from these cells. The JNK pathway therefore regulates production of this key pro-inflammatory cytokine. Matrix metalloproteinases (MMPs) promote cartilage and bone erosion in rheumatoid arthritis, and generalized tissue destruction in other autoimmune diseases. Inducible expression of MMPs, including MMP-3 and MMP-9, type II and IV collagenases, are regulated via activation of the JNK pathway and AP-1 (Gum, R., Wang, H., Lengyel, E., Juarez, J., and Boyd, D. *Oncogene* 14:1481–1493, 1997). In human rheumatoid synoviocytes activated with TNFa, IL-1, or Fas ligand the JNK pathway is activated (Han Z., Boyle D. L., Aupperle K. R., Bennett B., Manning A. M., Firestein G. S. *J. Pharm. Exp. Therap.* 291:1–7, 1999; Okamoto K., Fujisawa K., Hasunuma T., Kobata T., Sumida T., and Nishioka K. *Arth &Rheum* 40: 919–92615, 1997). Inhibition of JNK activation results in decreased AP-1 activation and collagenase-1 expression (Han et al., supra). The JNK pathway therefore regulates MMP expression in cells involved in rheumatoid arthritis.

Inappropriate activation of T lymphocytes initiates and perpetuates many autoimmune diseases, including asthma, inflammatory bowel disease and multiple sclerosis. The JNK pathway is activated in T cells by antigen stimulation and CD28 receptor co-stimulation and regulates production of the growth factor IL-2 and cellular proliferation (Su B., Jacinto E., Hibi M., Kallunki T., Karin M., Ben-Neriah Y. *Cell* 77:727–736, 1994; Faris M., Kokot N., Lee L., and Nel A. E. *J. Biol. Chem.* 271:27366–27373, 1996). Peripheral T cells from mice genetically deficient in JNKK1 show decreased proliferation and IL-2 production after CD28 co-stimulation and PMA/Ca2+ ionophore activation, providing important validation for the role of the JNK pathway in these cells (Nishina H., Bachmann M., Oliveria-dos-Santos A. J., et al. *J. Exp. Med.* 186: 941–953, 1997). It is known that T cells activated by antigen receptor stimulation in the absence of accessory cell-derived co-stimulatory signals lose the capacity to synthesize IL-2, a state called clonal anergy. This is an important process by which autoreactive T cell populations are eliminated from the peripheral circulation. Of note, anergic T cells fail to activate the JNK pathway in response to CD3- and CD28-receptor co-stimulation, even though expression of the JNK enzymes is unchanged (Li W., Whaley C. D., Mondino A., and Mueller D. L. *Science* 271: 1272–1276, 1996). Recently, the examination of JNK-deficient mice revealed that the JNK pathway plays a key role in T cell activation and differentiation to T helper 1 and 2 cell types. JNK1 or JNK2 knockout mice develop normally and are phenotypically unremarkable. Activated naïve CD4+ T cells from these mice fail to produce IL-2 and do not proliferate well (Sabapathy, K, Hu, Y, Kallunki, T, Schreiber, M, David, J-P, Jochum, W, Wagner, E, Karin, M. *Curr Biol* 9: 116–125, 1999). It is possible to induce T cell differentiation in T cells from these mice, generating Th1 cells (producers of IFN-g and TNFβ) and Th2 effector cells (producers of IL-4, IL-5, IL-6, IL-10 and IL-13) [22,23]. Deletion of either JNK1 or JNK2 in mice resulted in a selective defect in the ability of Th1 effector cells to express IFNg. This suggests that JNK1 and JNK2 do not have redundant functions in T cells and that they play different roles in the control of cell growth, differentiation and death. The JNK pathway therefore, is an important point for regulation of T cell responses to antigen.

Cardiovascular disease (CVD) accounts for nearly one quarter of total annual deaths worldwide. Vascular disorders such as atherosclerosis and restenosis result from dysregulated growth of the vessel wall, restricting blood flow to vital organs. The JNK pathway is activated by atherogenic stimuli and regulates local cytokine and growth factor production in vascular cells (Yang, D D, Conze, D, Whitmarsh, A J, et al, *Immunity,* 9:575, 1998). In addition, alterations in blood flow, hemodynamic forces and blood volume lead to JNK activation in vascular endothelium, leading to AP-1 activation and pro-atherosclerotic gene expression (Aspenstrom P., Lindberg U., and Hall A. *Curr. Biol.* 6:70–77, 1996). Ischemia and ischemia coupled with reperfusion in the heart, kidney or brain results in cell death and scar formation, which can ultimately lead to congestive heart failure, renal failure or cerebral dysfunction. In organ transplantation, reperfusion of previously ischemic donor organs results in acute leukocyte-mediated tissue injury and delay of graft function. The JNK pathway is activated by ischemia and reperfusion (Li Y., Shyy J., Li S., Lee J., Su B., Karin M., Chien S *Mol. Cell. Biol.* 16:5947–5954, 1996), leading to the activation of JNK-responsive genes and leukcoyte-mediated tissue damage. In a number of different settings JNK activation can be either pro- or anti-apoptotic. JNK activation is correlated with enhanced apoptosis in cardiac tissues following ischemia and reperfusion (Pombo C M, Bonventre J V, Avruch J, Woodgett J R, Kyriakis J. M, Force T. *J. Biol. Chem.* 269:26546–26551, 1994).

Cancer is characterized by uncontrolled growth, proliferation and migration of cells. Cancer is the second leading cause of death with 500,000 deaths and an estimated 1.3 million new cases in the United States in 1996. The role of signal transduction pathways contributing to cell transformation and cancer is a generally accepted concept. The JNK pathway leading to AP-1 appears to play a critical role in cancer. Expression of c-jun is altered in early lung cancer and may mediate growth factor signaling in non-small cell lung cancer (Yin T., Sandhu G., Wolfgang C. D., Burrier A., Webb R. L., Rigel D. F. Hai T., and Whelan J. *J. Biol. Chem.* 272:19943–19950, 1997). Indeed, over-expression of c-jun in cells results in transformation, and blocking c-jun activity inhibits MCF-7 colony formation (Szabo E., Riffe M., Steinberg S. M., Birrer M. J., Linnoila R. I. *Cancer Res.* 56:305–315, 1996). DNA-damaging agents, ionizing radiation and tumor necrosis factor activate the JNK pathway. In addition to regulating c-jun production and activity, JNK activation can regulate phosphorylation of p53, and thus can modulate cell cycle progression (Chen T. K., Smith L. M., Gebhardt D. K., Birrer M. J., Brown P. H. *Mol. Carcinogenesis* 15:215–226, 1996). The oncogene BCR-Abl, associated with t(9,22) Philadelphia chromosome translocation of chronic myelogenous leukemia, activates JNK and leads to transformation of hematopoietic cells (Milne D. M., Campbell L. E., Campbell D. G., Meek D. W. *J. Biol. Chem.* 270:5511–5518, 1995). Selective inhibition of JNK activation by a naturally occurring JNK inhibitory protein, called JIP-1, blocks cellular transformation caused by BCR-Abl expression (Raitano A. B., Halpern J. R., Hambuch T. M., Sawyers C. L. *Proc. Nat. Acad. Sci USA* 92:11746–11750, 1995). Thus, JNK inhibitors may block transformation and tumor cell growth.

Accordingly, there is a need in the art for selective inhibitors of JNK, as well as for methods for preparation thereof, pharmaceutical compositions comprising such inhibitors, and methods of inhibiting JNK's and treating diseases in mammals which are responsive to JNK inhibition. The present invention fulfills these needs, and provides further related advantages.

SUMMARY OF THE INVENTION

In brief, the present invention is directed to compounds having activity as selective inhibitors of JNK, as well as to compositions and methods related thereto. The compounds of the present invention (also referred to herein as "JNK inhibitors") may generally be classified as "pyrazoloanthrone derivatives" having the following structure (I):

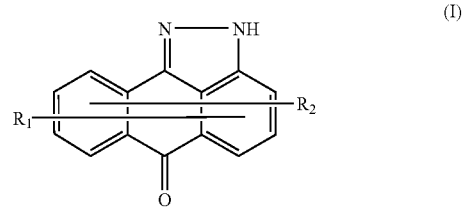

wherein $R_1$ and $R_2$ are as defined below, including pharmaceutically acceptable salts thereof.

The present invention is also directed to methods for treating a variety of conditions by administering an effective amount of a JNK inhibitor to an animal or subject in need thereof (referred to herein as a "patient"), typically a warm-blooded animal (including a human). Prior to administration, the compounds of this invention are preferably formulated as a pharmaceutical composition which contains an effective dosage amount of one or more JNK inhibitors in combination with one (or more) pharmaceutically acceptable carrier(s). Conditions that may be treated by the compounds of this invention, or a pharmaceutical composition containing the same, include any condition which may benefit from administration of JNK inhibitors, and are particularly useful for the prevention and/or treatment of various diseases including (but not limited to) rheumatoid arthritis, rheumatoid spondylitis, osteoarthritis, gout, asthma, bronchitis, cystic fibrosis, inflammatory bowel disease, irritable bowel syndrome, mucous colitis, ulcerative colitis, Crohn's disease, gastritis, esophagitis, hepatitis, multiple sclerosis, atherosclerosis, restenosis following angioplasty, left ventricular hypertrophy, myocardial infarction, stroke, ischemic damages to heart, kidney, liver, and brain, transplant rejection, endotoxin shock, psoriasis, eczema, dermatitis, epilepsy, Alzheimer's disease, Huntington's disease, Amyotrophic laterial sclerosis, peripheral neuropathies, spinal cord damage, Parkinson's disease, and cancer.

These and other aspects of this invention will be apparent upon reference to the following detailed description. To that end, certain patent and other documents are cited herein to more specifically set forth various aspects of this invention. Each of these documents are hereby incorporated by reference in their entirety.

DETAILED DESCRIPTION OF THE INVENTION

Figure 1:
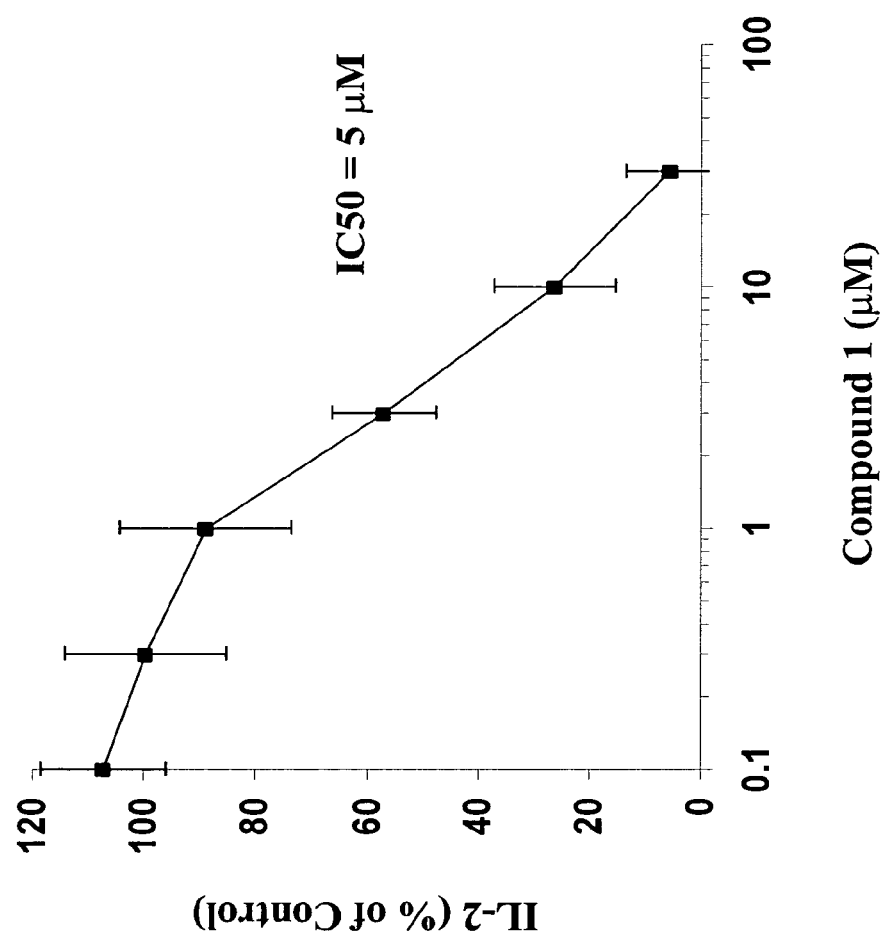
FIG. 1 illustrates the ability of a representative compound of this invention to inhibit IL-2 in Jurkat T-Cell.

As mentioned above, the present invention is directed to compounds which have activity as selective inhibitors of JNK, as well as to compositions and methods relating to the same. The compounds of this invention have the following structure (I):

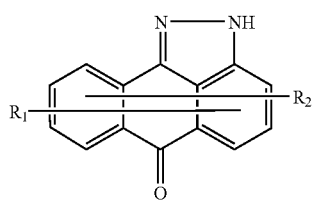

and pharmaceutically acceptable salts thereof, wherein:

$R_1$ and $R_2$ are optional substituents that are the same or different and independently represent alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono- or di-alkylaminoalkoxy, or a group represented by formula (a), (b), (c) or (d):

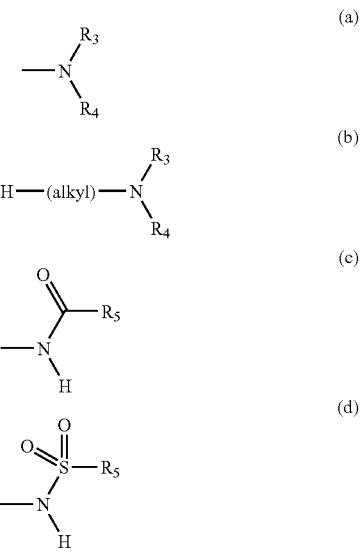

$R_3$ and $R_4$ taken together represent alkylidene or a heteroatom-containing alkylidene, or $R_3$ and $R_4$ are the same or different and independently represent hydrogen, alkyl, cycloalkyl, aryl, arylalkyl, cycloalkylalkyl, aryloxyalkyl, alkoxyalkyl, alkoxyamino, or alkoxy(mono- or di-alkylamino); and $R_5$ represents hydrogen, alkyl, cycloalkyl, aryl, arylalkyl, cycloalkylalkyl, alkoxy, amino, mono- or di-alkylamino, arylamino, arylalkylamino, cycloalkylamino, or cycloalkylalkylamino.

As used herein, the terms used above having following meaning.

"Alkyl" means a straight chain or branched, saturated or unsaturated alkyl chain having from 1 to 8 carbon atoms, such as methyl, ethyl, n-propyl, iso-propyl, n-butyl, iso-butyl, tert-butyl, propylenyl, 1-butenyl, propynyl, and the like.

"Halogen" means fluorine, chlorine, bromine or iodine.

"Trifluoromethyl" means —$CF_3$.

"Sulfonyl" means —$SO_3H$;

"Carboxyl" means —COOH.

"Alkoxy" means —O-(alkyl), such as methoxy, ethoxy, n-propyloxy, iso-propyloxy, n-butyloxy, iso-butyloxy, and the like.

"Alkoxyalkoxy" means —O-(alkyl)-O-(alkyl), such as —$OCH_2CH_2OCH_3$, and the like.

"Alkoxycarbonyl" means —C(|O)O-(alkyl), such as —C(=O)$OCH_3$, —C(=O)$OCH_2CH_3$, and the like.

"Alkoxyalkyl" means -(alkyl)-O-(alkyl), such as —$CH_2OCH_3$, —$CH_2OCH_2CH_3$, and the like.

"Aryl" means a carbocyclic or heterocyclic aromatic group containing from 5 to 10 ring atoms. The ring atoms of a carbocyclic aryl group are all carbon atoms, and includes phenyl and naphthyl. The ring atoms of a heterocyclic aryl group contains at least one heteroatom selected from nitrogen, oxygen and sulfur, and include pyridinyl, pyrimidinyl, furanyl, thienyl, imidazolyl, thiazolyl, pyrazolyl, pyridazinyl, pyrazinyl, triazinyl, tetrazolyl, and indolyl.

"Aryloxy" means —O-(aryl), such as —O-phenyl, —O-pyridinyl, and the like.

"Arylalkyl" means -(alkyl)-(aryl), such as benzyl (i.e., —$CH_2$phenyl), —$CH_2$-pyrindinyl, and the like.

"Arylalkyloxy" means —O-(alkyl)-(aryl), such as —O-benzyl, —O—CH$_2$-pyridinyl, and the like.

"Cycloalkyl" means a cyclic alkyl having from 3 to 7 carbon atoms, such as cyclopropyl, cyclopentyl, cyclohexyl, and the like.

"Cycloalkyloxy" means —O-(cycloalkyl), such as —O-cyclohexyl, and the like.

"Cycloalkylalkyloxy" means —O-(alkyl)-(cycloalkyl, such as —OCH$_2$cyclohexyl, and the like.

"Alkylidene" means the divalent radical —CH$_n$H$_{2n}$—, wherein n is an integer from 1 to 8, such as —CH$_2$—, —CH$_2$CH$_2$—, —CH$_2$—CH$_2$—CH$_2$—, —CH$_2$CH$_2$CH$_2$CH$_2$—, —CH$_2$CH$_2$CH$_2$CH$_2$CH$_2$—, and the like.

"Heteroatom-containing alkylidene" means an alkylidene wherein at least one carbon atom is replaced by a heteroatom selected from nitrogen, oxygen or sulfur, such as —CH$_2$CH$_2$OCH$_2$CH$_2$—, and the like.

"Aminoalkoxy" means —O-(alkyl)-NH$_2$, such as —OCH$_2$NH$_2$, —OCH$_2$CH$_2$NH$_2$, and the like.

"Mono- or di-alkylamino" means —NH(alkyl) or —N(alkyl)(alkyl), respectively, such as —NHCH$_3$, —N(CH$_3$)$_2$, and the like.

"Mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like.

"Arylamino" means —NH(aryl), such as —NH-phenyl, —NH-pyridinyl, and the like.

"Arylalkylamino" means —NH-(alkyl)-(aryl), such as —NH-benzyl, —NHCH$_2$-pyridinyl, and the like.

"Alkylamino" means —NH(alkyl), such as —NHCH$_3$, —NHCH$_2$CH$_3$, and the like.

"Cycloalkylamino" means —NH-(cycloalkyl), such as —NH-cyclohexyl, and the like.

"Cycloalkylalkylamino" —NH-(alkyl)-(cycloalkyl), such as —NHCH$_2$-cyclohexyl, and the like.

In the embodiment wherein R$_1$ and R$_2$ are not present, compounds of this invention have the following structure (II) (also referred to herein as "Compound 1"):

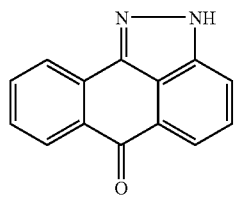

(II)

This compound is commercially available from Pfaltz-Bauer (Conn., U.S.).

In the embodiment wherein only one of R$_1$ and R$_2$ is present, compounds of this invention have one of the following structures (III) or (IV):

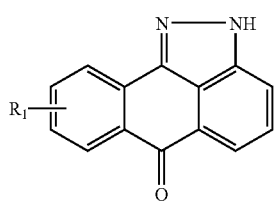

(III)

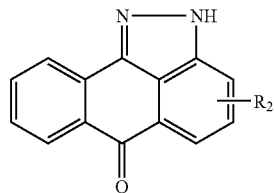

(IV)

In the embodiment wherein both R$_1$ and R$_2$ are present, compounds of this invention have one of the following structures (V), (VI) or (VII):

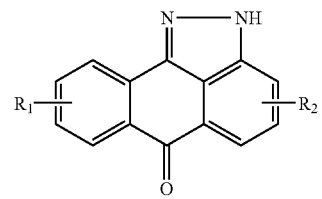

(V)

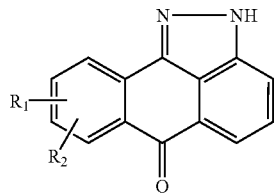

(VI)

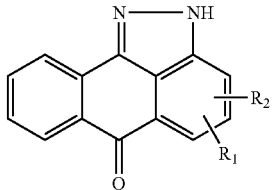

(VII)

Pharmaceutically acceptable salts of compounds of structure (I) are also within the scope of this invention. To this end, the compound may generally be utilized as the free base. Alternatively, the compounds may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of a compound of structure (I) is intended to encompass any and all acceptable salt forms.

The compounds of this invention may generally be made by organic synthesis techniques known to those skilled in the art, as well as by the following general techniques and by the procedures set forth in the Examples. To that end, the compounds of this invention may be made according to the following Reaction Schemes 1 through 7.

Reaction Scheme 1

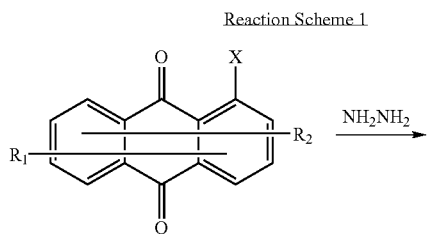

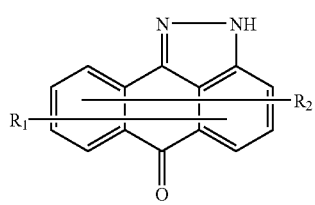

In Reaction Scheme 1, pyrazoloanthrones of this invention may be prepared by condensation of appropriate anthraquinones having a leaving group at the 1-position (such as fluoro, chloro, bromo, iodo, nitro, methanesulfonyloxy, tosyloxy or phenoxy) with hydrazine in a suitable solvent (such as pyridine, dimethylformamide, methylene chloride, chloroform, or dioxane). The reaction is carried out at temperatures ranging 0° C. to 200° C. for 1 to 16 hours. Suitable anthraquinone starting materials are commercially available from a variety of sources with the $R_1$ and/or $R_2$ groups at various positions on the anthraquinone ring. For purpose of illustration, the following reaction schemes depict synthesis of 5- and/or 7-substituted pyrazoloanthrones. One skilled in the art will recognize that pyrazoloanthrones substituted at other positions may be made in a similar manner from the appropriately substituted pyrazoloanthrone starting material.

Reaction Scheme 2

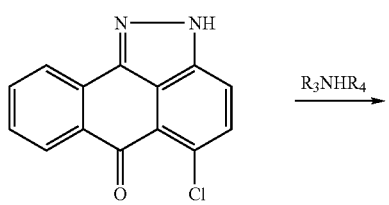

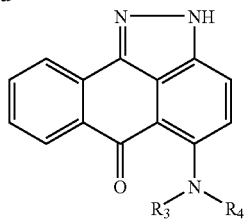

In Reaction Scheme 2, pyrazoloanthrones with 5-amino substituents may be prepared by condensation of 5-chloro-pyrazoloanthrone with mono- or disubstituted amines at 0 to 250° C. for 1 to 16 hours, either in the absence or the presence of a solvent. Typically solvents are pyridine, dimethylformamide, dimethylsulfoxide, dichloroethane, chloroform, tetrahydrofuran, dioxane, diglyme, or triglyme in the presence of excess amount of the amine, or in the presence of an acid quenching agent such as triethylamine, diisopropylethylamine, sodium bicarbonate, potassium carbonate, or sodium hydroxide.

Reaction Scheme 3

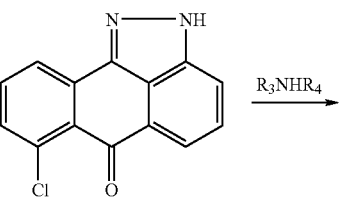

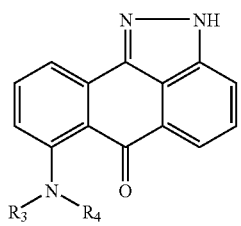

In Reaction Scheme 3, pyrazoloanthrones with 7-amino substituents may be prepared by condensation of 7-chloro-pyrazoloanthrone with mono- or disubstituted amines at 0 to 250° C. for 1 to 16 hours either in the absence or the presence of a solvent. Typically solvents are pyridine, dimethylformamide, dimethylsulfoxide, dichloroethane, chloroform, tetrahydrofuran, dioxane, diglyme, or triglyme in the presence of excess amount of the amine, or in the presence of an acid quenching agent such as triethylamine, diisopropylethylamine, sodium bicarbonate, potassium carbonate, or sodium hydroxide.

Reaction Scheme 4

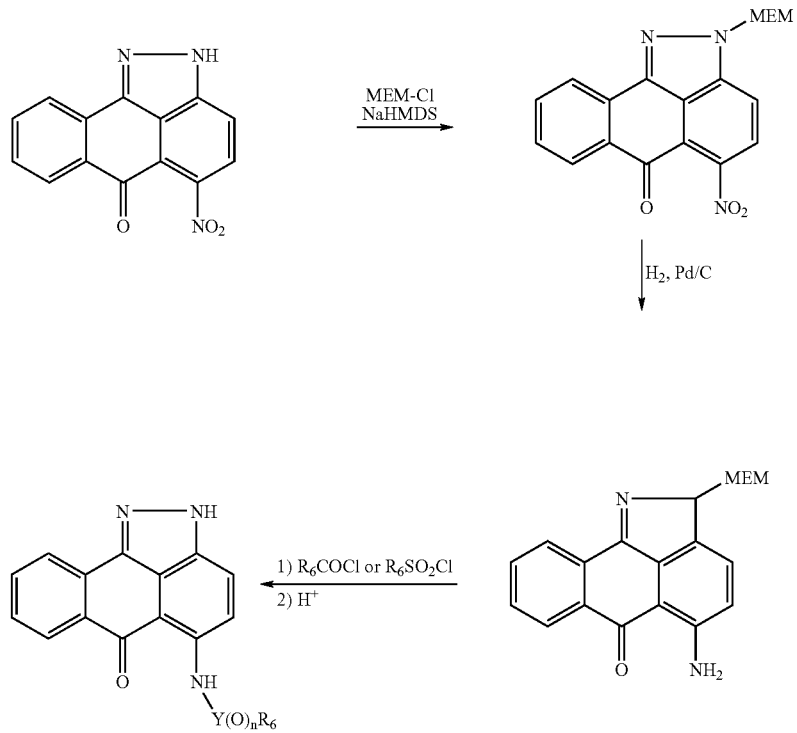

Y = C, n = 1
Y = S, n = 2

In Reaction Scheme 4, pyrazoloanthrones with 5-acyl- or sulfonylamino substituents may be prepared by condensation of 5-amino-2-(2-methoxyethoxymethyl)pyrazoloanthrone with acid chlorides and sulfonyl chlorides followed by the deprotection. Condensation of 5-amino-2-(2-methoxyethoxymethyl)pyrazoloanthrone with appropriate acid chlorides $R_6COCl$ or sulfonyl chlorides $R_6SO_2Cl$ is carried out in the presence of an acid quenching agent such as triethylamine, diisopropylethylamine, sodium bicarbonate, potassium carbonate, or sodium hydroxide at −20 to 50° C. for 0.5 to 16 hours in solvents such as methylene chloride, chloroform, tetrahydrofuran, dioxane, dimethylformamide, and ethyl acetate. The deprotection step may be performed by the treatment of the product mentioned above with an acid such as trifluoroacetic acid, aqueous hydrochloric acid, aqueous hydrobromic acid, or aqueous sulfuric acid.

The starting material may be prepared in two steps. The 2-position of 5-nitropyrazoloanthrone may be protected by a protective group such as methoxymethyl (MOM), methoxyethoxymethyl (MEM), 2-trimethylsilylethoxymethyl (SEM), or 4-methoxybenzyl (PMB) with an aid of a base such as triethylamine, diisopropylethylamine, pyridine, sodium hexamethyldisilazide, potassium hexamethyldisilazide, or lithium diisopropylamide. 4-(N, N-dimethylamino)pyridine (DMAP) may be used as a catalyst when a tertiary amine is used as a base. The reaction is typically carried out at −40 to 60° C. for 1 to 16 hours in a solvent such as methylene chloride, chloroform, tetrahydrofuran, dioxane, or dimethoxyethane. As the nitrogen protective group, MEM group is preferred.

N-Protected 5-nitropyrazoloanthorone is then reduced to its 5-amino derivative by a variety of reducing agents such as Sn or Fe metal in acidic media such as acetic acid or aqueous hydrochloric acid. The reaction is typically run at 20 to 160° C. for 1 to 16 hours. The same transformation can be carried out by hydrogenation in the presence of a transition-metal catalyst such as palladium, platinum, rhodium, or iridium with or without a support such as charcoal in a solvent such as ethanol, ethyl acetate, tetrahydrofuran, dioxane, or dimethoxyethane at 1 to 20 atmospheres of hydrogen at 20 to 60° C. for 1 to 16 hours. The procedure using hydrogenation with palladium on charcoal as the catalyst is preferred.

Reaction Scheme 5

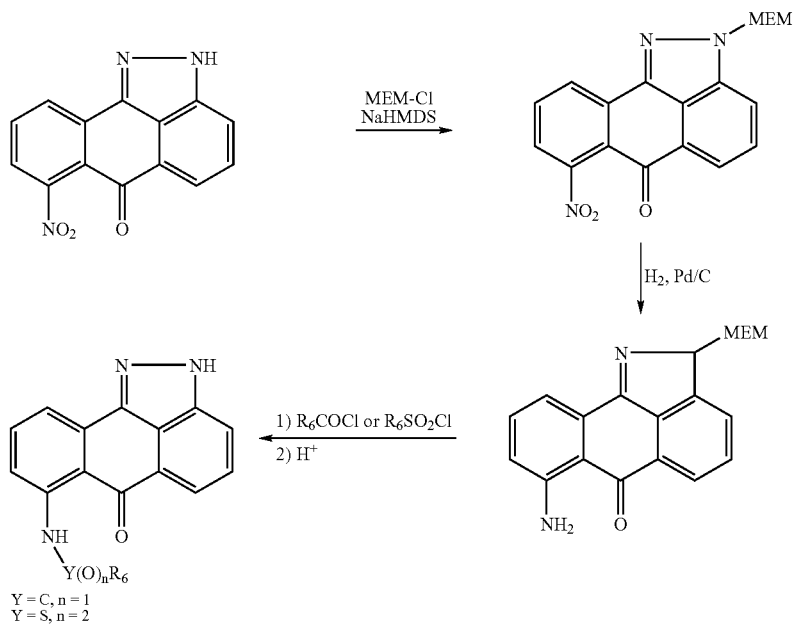

In Reaction Scheme 5, pyrazoloanthrones with 7-acyl- or sulfonylamino substituents may be prepared by condensation of 7-amino-2-(2-methoxyethoxymethyl)pyrazoloanthrone with acid chlorides and sulfonyl chlorides followed by the deprotection. Condensation of 7-amino-2-(2-methoxyethoxymethyl)pyrazoloanthrone with appropriate acid chlorides $R_6COCl$ or sulfonyl chlorides $R_6SO_2Cl$ is carried out in the presence of an acid quenching agent such as triethylamine, diisopropylethylamine, sodium bicarbonate, potassium carbonate, or sodium hydroxide at –20 to 50° C. for 0.5 to 16 hours in solvents such as methylene chloride, chloroform, tetrahydrofuran, dioxane, dimethylformamide, or ethyl acetate. The deprotection step may be performed by the treatment of the product mentioned above with an acid such as trifluoroacetic acid, aqueous hydrochloric acid, aqueous hydrobromic acid, or aqueous sulfuric acid.

The starting material is prepared in two steps. The 2-position of 7-nitropyrazoloanthrone is protected by a protective group such as methoxymethyl (MOM), methoxyethoxymethyl (MEM), 2-trimethylsilylethoxymethyl (SEM), or 4-methoxybenzyl (PMB) with an aid of a base such as triethylamine, diisopropylethylamine, pyridine, sodium hexamethyldisilazide, potassium hexamethyldisilazide, or lithium diisopropylamide. 4-(N, N-dimethylamino)pyridine (DMAP) can be used as a catalyst when a tertiary amine is used as a base. The reaction is typically carried out at –40 to 60° C. for 1 to 16 hours in a solvent such as methylene chloride, chloroform, tetrahydrofuran, dioxane, or dimethoxyethane. As the nitrogen protective group, MEM group is preferred.

N-Protected 7-nitropyrazoloanthorone is then reduced to its 7-amino derivative by a variety of reducing agents such as Sn or Fe metal in acidic media such as acetic acid or aqueous hydrochloric acid. The reaction is typically run at 20 to 160° C. for 1 to 16 hours. The same transformation can be carried out by hydrogenation in the presence of a transition-metal catalyst such as palladium, platinum, rhodium, or iridium with or without a support such as charcoal in a solvent such as ethanol, ethyl acetate, tetrahydrofuran, dioxane, or dimethoxyethane at 1 to 20 atmospheres of hydrogen at 20 to 60° C. for 1 to 16 hours. The procedure using hydrogenation with palladium on charcoal as the catalyst is preferred.

Reaction Scheme 6

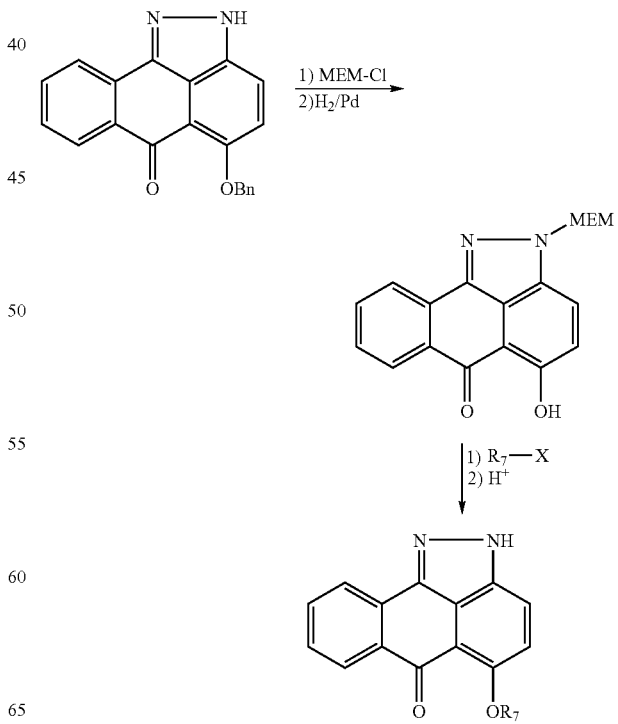

In Reaction Scheme 6, pyrazoloanthrones with 5-alkoxy substituents may be prepared by condensation of 5-hydroxy-2-(2-methoxyethoxymethyl)-pyrazoloanthrone with alkyl halides and sulfonates $R_7$-X followed by the deprotection. As the leaving group X, chloride, bromide, iodide, methanesulfonate, tosylate, benzenesulfonate, or triflate can be used. Condensation of 5-hydroxy-2-(2-methoxyethoxymethyl)pyrazoloanthrone with appropriate alkyl halides and sulfonates is carried out in the presence of an acid quenching agent such as triethylamine, diisopropylethylamine, sodium bicarbonate, potassium carbonate, or sodium hydroxide at −20 to 50° C. for 0.5 to 16 hours in solvents such as methylene chloride, chloroform, tetrahydrofuran, dioxane, dimethylformamide, or ethyl acetate. The deprotection step is performed by the treatment of the product mentioned above with an acid such as trifluoroacetic acid, aqueous hydrochloric acid, aqueous hydrobromic acid, or aqueous sulfuric acid.

The starting material is prepared in two steps. The 2-position of 5-benzyloxypyrazoloanthrone is protected by a protective group such as methoxymethyl (MOM), methoxyethoxymethyl (MEM), 2-trimethylsilylethoxymethyl (SEM), or 4-methoxybenzyl (PMB) with an aid of a base such as triethylamine, diisopropylethylamine, pyridine, sodium hexamethyldisilazide, potassium hexamethyldisilazide, or lithium diisopropylamide. 4-(N, N-dimethylamino)pyridine (DMAP) can be used as a catalyst when a tertiary amine is used as a base. The reaction is typically carried out at −40 to 60° C. for 1 to 16 hours in a solvent such as methylene chloride, chloroform, tetrahydrofuran, dioxane, or dimethoxyethane. As the nitrogen protective group, MEM group is preferred.

N-Protected 5-benzyloxypyrazoloanthorone is then reduced to its 5-hydroxy derivative by hydrogenation in the presence of a transition-metal catalyst, such as palladium platinum, rhodium, or iridium with or without a support such as charcoal in a solvent such as ethanol, ethyl acetate, tetrahydrofuran, dioxane, or dimethoxyethane at 1 to 20 atmospheres of hydrogen at 20 to 60° C. for 1 to 16 hours. The procedure using hydrogenation with palladium on charcoal as the catalyst is preferred.

Reaction Scheme 7

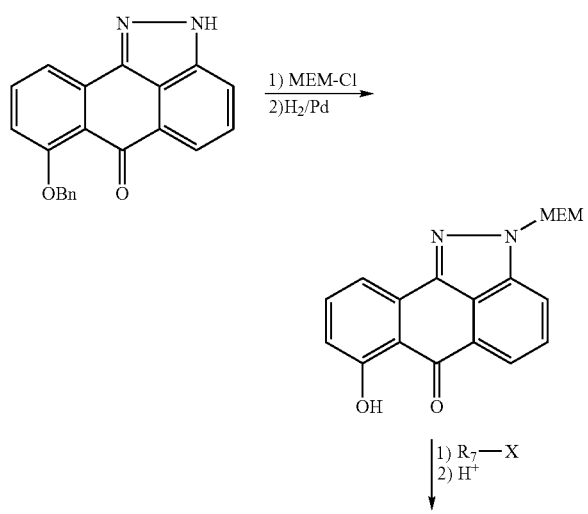

-continued

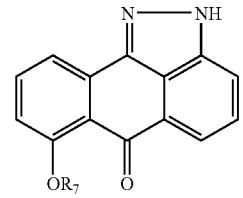

In Reaction Scheme 7, pyrazoloanthrones with 5-alkoxy substituents may be prepared by condensation of 7-hydroxy-2-(2-methoxyethoxymethyl)-pyrazoloanthrone with alkyl halides and sulfonates $R_7$-X followed by the deprotection. As the leaving group X, chloride, bromide, iodide, methanesulfonate, tosylate, benzenesulfonate, or triflate can be used. Condensation of 7-hydroxy-2-(2-methoxyethoxymethyl)pyrazoloanthrone with appropriate alkyl halides and sulfonates is carried out in the presence of an acid quenching agent such as triethylamine, diisopropylethylamine, sodium bicarbonate, potassium carbonate, or sodium hydroxide at −20 to 50° C. for 0.5 to 16 hours in solvents such as methylene chloride, chloroform, tetrahydrofuran, dioxane, dimethylformamide, or ethyl acetate. The deprotection step is performed by the treatment of the product mentioned above with an acid such as trifluoroacetic acid, aqueous hydrochloric acid, aqueous hydrobromic acid, or aqueous sulfuric acid.

The starting material is prepared in two steps. The 2-position of 7-benzyloxypyrazoloanthrone is protected by a protective group such as methoxymethyl (MOM), methoxyethoxymethyl (MEM), 2-trimethylsilylethoxymethyl (SEM), or 4-methoxybenzyl (PMB) with an aid of a base such as triethylamine, diisopropylethylamine, pyridine, sodium hexamethyldisilazide, potassium hexamethyldisilazide, or lithium diisopropylamide. 4-(N, N-dimethylamino)pyridine (DMAP) can be used as a catalyst when a tertiary amine is used as a base. The reaction is typically carried out at −40 to 60° C. for 1 to 16 hours in a solvent such as methylene chloride, chloroform, tetrahydrofuran, dioxane, or dimethoxyethane. As the nitrogen protective group, MEM group is preferred.

N-Protected 7-benzyloxypyrazoloanthorone is then reduced to its 7-hydroxy derivative by hydrogenation in the presence of a transition-metal catalyst, such as palladium platinum, rhodium, or iridium with or without a support such as charcoal in a solvent such as ethanol, ethyl acetate, tetrahydrofuran, dioxane, or dimethoxyethane at 1 to 20 atmospheres of hydrogen at 20 to 60° C. for 1 to 16 hours. The procedure using hydrogenation with palladium on charcoal as the catalyst is preferred.

Compounds of structures (V), (VI) and (VII) may be made by the same procedures as outlined above by utilizing starting materials having multiple reactive sites at the corresponding positions to the desired product.

In another embodiment of the invention, pharmaceutical compositions containing one or more compounds of this invention are disclosed. For purpose of administration, a compound of structure (I) is preferably formulated as a pharmaceutical composition. Pharmaceutical compositions of the present invention comprise a compound of this invention and a pharmaceutically acceptable carrier, wherein the compound is present in the composition in an amount which is effective to treat the condition of interest. Preferably, the pharmaceutical compositions of the present invention include a compound of structure (I) in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating a variety of conditions by administering an effective amount of a JNK inhibitor to a patient in need thereof. Conditions that may be treated by the compounds of this invention, or a pharmaceutical composition containing the same, include any condition which is responsive to JNK inhibition, and thereby benefit from administration of a JNK inhibitor. Representative conditions in this regard include (but not limited to) rheumatoid arthritis, rheumatoid spondylitis, osteoarthritis, gout, asthma, bronchitis, cystic fibrosis, inflammatory bowel disease, irritable bowel syndrome, mucous colitis, ulcerative colitis, Crohn's disease, gastritis, esophagitis, hepatitis, multiple sclerosis, atherosclerosis, restenosis following angioplasty, left ventricular hypertrophy, myocardial infarction, stroke, ischemic damage to the heart, kidney, liver, or brain, transplant rejection (such as kidney, liver, heart, lung, and the like), endotoxin shock, psoriasis, eczema, dermatitis, epilepsy, Alzheimer's disease, Parkinson's disease, Huntington's disease, amyotrophic lateral sclerosis, peripheral neuropathies, spinal cord damage, and cancer.

The methods of this invention include systemic administration of a compound of this invention, preferably in the form of a pharmaceutical composition. As used herein, systemic administration encompasses both oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain buffers, antioxidants, bacteriostats, and other additives commonly employed in such solutions.

The following examples are offered by way of illustration, not limitation.

EXAMPLES

Example 1

Synthesis of Representative Compounds

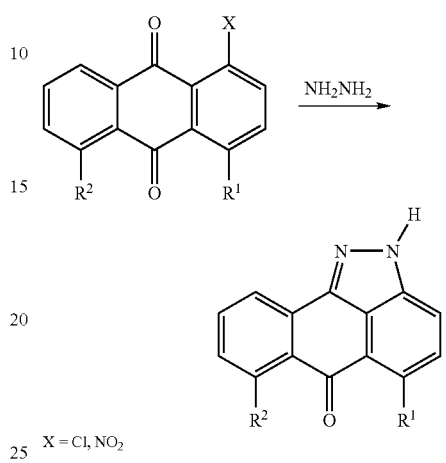

$X = Cl, NO_2$

A. Anthra[1,9cd]pyrazol-6(2H)-one ("Compound 1")

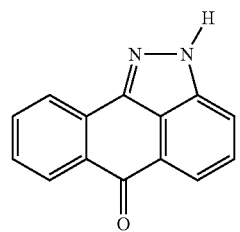

Anhydrous hydrazine is added to a solution of 2-chloroanthraquinone (Aldrich) in 10 mL pyridine, and the mixture heated at 100° C. for 16 hours. The mixture is cooled and the solvent is evaporated in vacuo. The residue is taken in hot 6N HCl, and the solid is collected by filtration. Flash chromatography of the crude material on silica gel affords anthra[1,9cd]pyrazol-6(2H)-one ("Compound 1") as yellow solids.

Due to limited solubility of Compound 1, purification of the same may be achieved by first derivatizing Compound 1 to a more soluble intermediate, such as the corresponding acetate, recrystallizing the intermediate, and then converting the intermediate to yield purified Compound 1 in good yield. More specifically, to solution of the pyrazoloanthrone (9.67 g, 43.9 mmol) in acetic acid (700 mL) is added acetic anhydride (12.4 mL, 132 mmol). The solution is heated to 80° C. for 5 hours and then cooled to room temperature. After 16 hours, the reaction is cooled to 0° C. for 2 hours. The reaction is then filtered to give the N-acetylpyrazoloanthrone intermediate. This intermediate is recrystallized in acetic acid to give the pure intermediate (5.96 g, 52%). $^1$H NMR (CDCL$_3$) δ 10.6 (br s, 1H), 8.46 (d, 1H), 8.33 (d, 1H), 8.26 (d, 1H), 8.08 (d, 1H), 7.96–7.87 (m, 2H), 7.78 (t, 1H), 2.83 (s, 3H); ES-MS (m/z) 263 [M+1]$^+$. To a solution of the pure intermediate (5.96 g, 23 mmol) in methanol (600 mL) is added ammonium hydroxide (60 mL). The reaction is stirred at room temperature for 16 hours and then filtered and dried in a vacuum oven. A second crop of crystals is recovered to give a total of 4.8 g of Compound 1 at greater than 98% purity. ES-MS (m/z) 221 [M+1]⁺.

B. 5-Chloroanthra[1,9cd]pyrazol-6(2H)-one

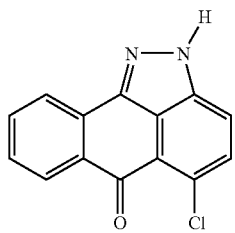

This compound may be made in the same manner from 1,4-dichloroanthraquinone (commercial product).

C. 7-Chloroanthra[1,9cd]pyrazol-6(2H)-one

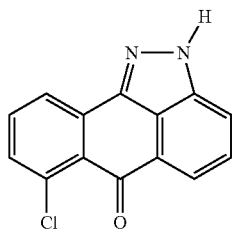

This compound may be made in the same manner from 1,5-dichloroanthraquinone (commercial product).

D. 5-Nitroanthra[1,9cd]pyrazol-6(2H)-one

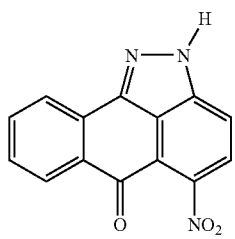

This compound may be made from 1,4-dinitroanthraquinone (Krapcho, A. P.; Avery, K. L., Jr. *J. Org. Chem.* 55, 5562–4, 1990).

E. 7-Nitroanthra[1,9cd]pyrazol-6(2H)-one

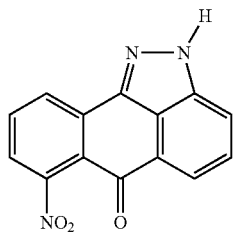

This compound may be made in the same manner from 1,5-dichloroanthraquinone (commercial product).

F. 5-Benzyloxyanthra[1,9cd]pyrazol-6(2H)-one

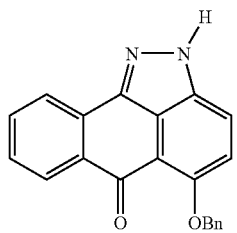

This compound may be made in the same manner from 1-nitro-4-benzyloxyanthraquinone. This starting material may be prepared as follows. Benzyl bromide is added to 1-nitro-4-hydroxyanthraquinone (Aldrich) and potassium carbonate in dimethylformamide, and the mixture is stirred for 16 hours. Water is added and the mixture is extracted with ethyl acetate (×2). The combined organic layer is washed sequentially with sodium bicarbonate solution, water, 1N hydrochloric acid, and brine, dried, and evaporated. The residue is chromatographed on silica gel to afford 1-nitro-4-benzyloxyanthraquinone.

G. 7-Benzyloxyanthra[.1,9cd]pyrazol-6(2H)-one

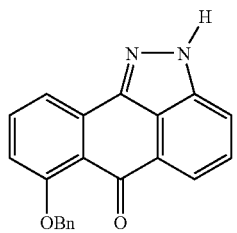

This compound may be made in the same manner from 1-nitro-5-benzyloxyanthraquinone, which starting material may prepared as disclosed in German Patent No. DE 2254199 to Reubke, Hohmann and Bien.

H. 5-(Acetylamino)anthra[1,9cd]pyrazol-6(2H)-one

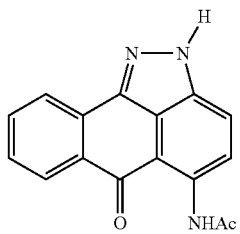

This compound may be made in the same manner from 4-acetylamino-1-chloroanthraquinone. This starting material may be prepared as follows. 4-Amino-1-chloroanthraquinone is taken in pyridine and treated with acetic anhydride. The mixture is stirred for 1 hour, and poured onto water. The solids are collected by filtration, washed with water, and dried in vacuo to give 4-acetylamino-1-chloroanthraquinone as a colorless solid.

Example 2

Synthesis of Representative Compounds

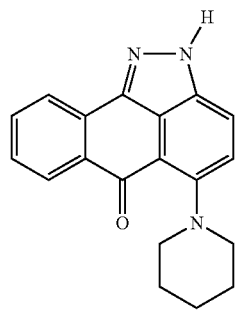

A.
5-(Dimethylamino)anthra[1,9cd]pyrazol-6(2H)-one

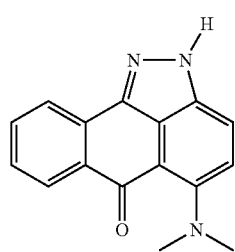

A mixture of 5-chloroanthra[1,9cd]pyrazol-6(2H)-one (Example 1-B) and dimethylamine in pyridine is heated at 100° C. for 16 hours. The mixture is cooled and evaporated. The residue is chromatographed on silica gel to give the desired compound as yellow solids.

B. 5-(1-Piperidinyl)anthra[1,9cd]pyrazol-6(2H)-one

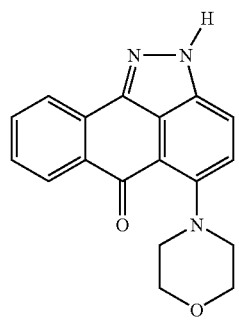

This compound may be made in the same manner using piperidine as the amine.

C.
5-(1-Morpholinyl)anthra[1,9cd]pyrazol-6(2H)-one

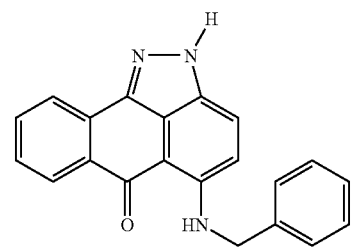

This compound may be made in the same manner using morpholine as the amine.

D. 5-(Benzylamino)anthra[1,9cd]pyrazol-6(2H)-one

This compound may be made in the same manner using benzylamine as the amine.

E. 5-{(4-Pyridylmethyl)lamino}anthra[1,9cd]pyrazol-6(2H)-one

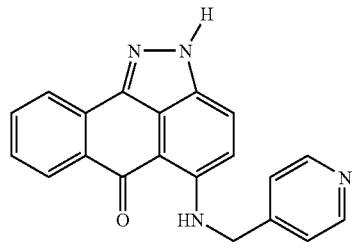

This compound may be made in the same manner using 4-pyridylmethylamine as the amine.

F. 5-{2-(1-Piperidinyl)ethylamino}anthra[1,9cd]pyrazol-6(2H)-one

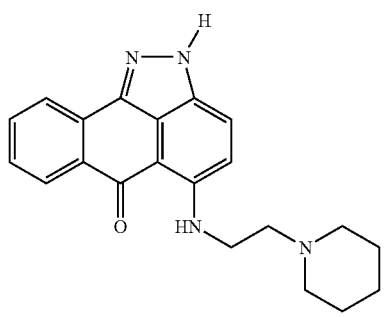

This compound may be made in the same manner using 2-(1-piperidyl)ethylamine as the amine.

Example 3

Synthesis of Representative Compounds

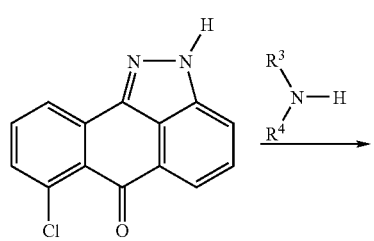

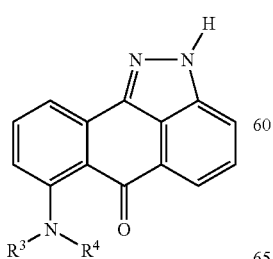

A. 7-(Dimethylamino)anthra[1,9cd]pyrazol-6(2H)-one

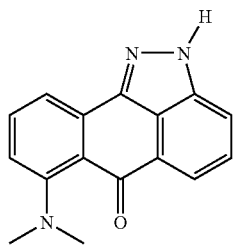

A mixture of 6-chloroanthra[1,9cd]pyrazol-6(2H)-one (Example 1-C) and dimethylamine in pyridine is heated at 100° C. for 16 hours. The mixture is cooled and evaporated. The residue is chromatographed on silica gel to give the desired compound as yellow solids.

B. 5-(1-Piperidinyl)anthra[1,9cd]pyrazol-6(2H)-one

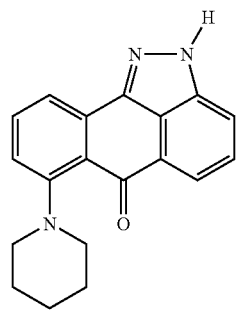

This compound may be made in the same manner using piperidine as the amine.

C. 5-(1-Morpholinyl)anthra[1,9cd]pyrazol-6(2H)-one

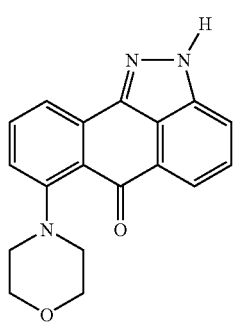

This compound may be made in the same manner using morpholine as the amine.

D. 5-(Benzylamino)anthra[1,9cd]pyrazol-6(2H)-one

This compound may be made in the same manner using benzylamine as the amine.

E. 5-{(4-Pyridylmethyl)lamino}anthra[1,9cd]pyrazol-6(2H)-one

This compound may be made in the same manner using 4-pyridylmethylamine as the amine.

F. 5-{2-(1-Piperidinyl)ethylamino}anthra[1,9cd]pyrazol-6(2H)-one

This compound may be made in the same manner using 2-(1-piperidyl)ethylamine as the amine.

Example 4

Synthesis of Representative Compounds

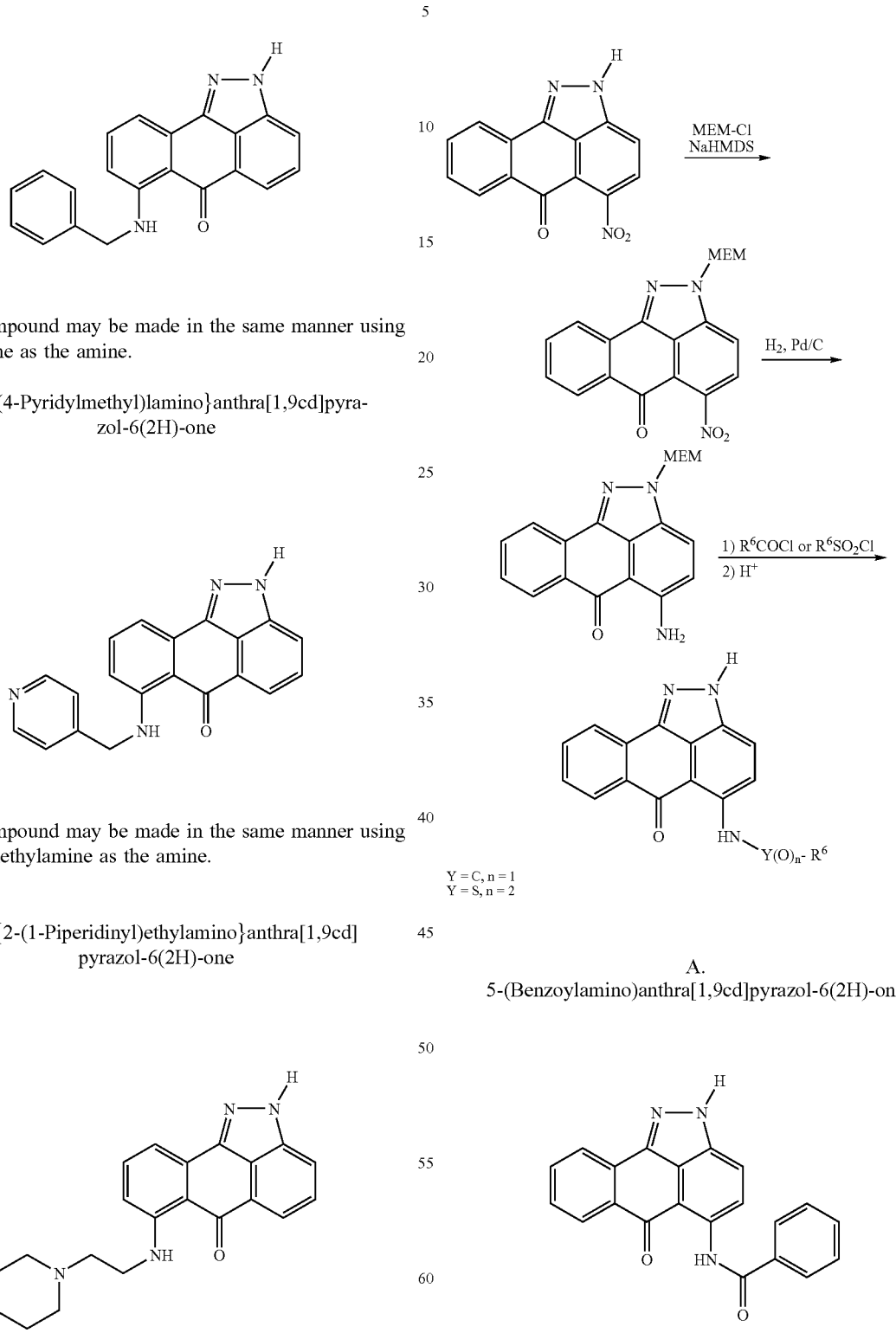

Y = C, n = 1
Y = S, n = 2

A. 5-(Benzoylamino)anthra[1,9cd]pyrazol-6(2H)-one

Benzoyl chloride is added to a solution of 2-(methoxyethoxymethyl)-5-aminoanthra[1,9cd]pyrazol-6-(2H)one and triethylamine in methylene chloride at 0° C. The mixture is stirred for 16 hours, quenched with water, and extracted with ethyl acetate (×2). The combined organic layer is washed with sodium bicarbonate solution, and brine, dried and evaporated. The crude reaction mixture is then taken in aqueous 6N hydrochloric acid, and heated at 80° C. for 4 hours. After cooling, the mixture is extracted with ethyl acetate (×2), washed with brine, dried, and evaporated. The reside is chromatographed on silica gel to furnish the desired amide as a yellow solid.

The starting material is prepared as follows. Sodium hexamethyldisilazide is added to a cooled (0° C.) solution of 5-nitroanthra[1,9cd]pyrazol-6(2H)-one (Example 1-D) in tetrahydrofuran, and the mixture is stirred for 30 minutes at 0° C. MEM-chloride is added, and the mixture is stirred for 16 hours at room temperature. Water is added and the mixture is extracted with ethyl acetate (×2). The combined organic layer is washed with aqueous sodium bicarbonate solution, water, 1N hydrochloric acid, and brine, dried and evaporated. The residue is chromatographed on silica gel to give 2-MEM-5-nitroanthra[1,9cd]pyrazol-6(2H)-one as an oil.

Palladium(10%) on charcoal and 2-MEM-5-nitroanthra [1,9cd]pyrazol-6(2H)-one in ethanol is placed under 1-atm of hydrogen, and the mixture was stirred for 6 hours. The catalyst is filtered off over celite, and the filtrate is evaporated to dryness to give 2-(methoxyethoxymethyl)-5-aminoanthra[1,9cd]pyrazol-6-(2H)one, which is used without further purification.

B. 5-(Isonicotinylamino)anthra[1,9cd]pyrazol-6 (2H)-one

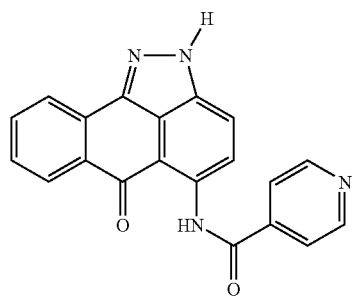

This compound may be made in the same manner using isonicotinoyl chloride as the acid chloride

C. 5-(Nicotinylamino)anthra[1,9cd]pyrazol-6(2H)-one

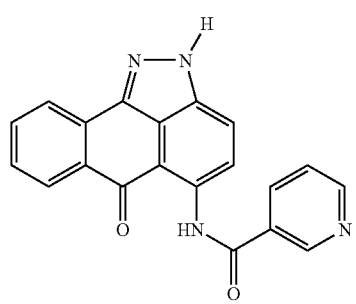

This compound may be made in the same manner using nicotinoyl chloride as the acid chloride.

D. 5-(2-Thiophenecarbonylamino)anthra[1,9cd] pyrazol-6(2H)-one

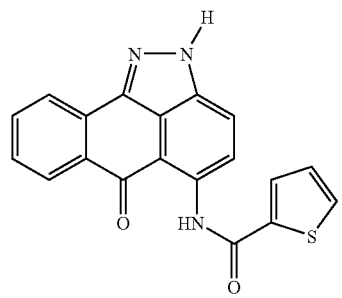

This compound may be made in the same manner using 2-thiophenecarboxylic acid as the acid chloride.

E. 5-(3-Methylbutyrylamino)anthra[1,9cd]pyrazol-6 (2H)-one

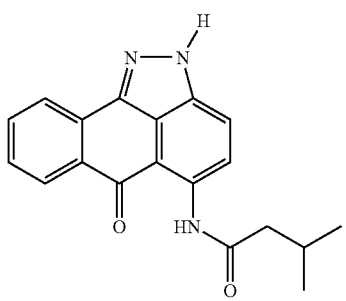

This compound may be made in the same manner using isopentanoyl chloride as the acid chloride.

F. 5-(3-Methanesulfonylamino)anthra[1,9cd]pyrazol-6(2H)-one

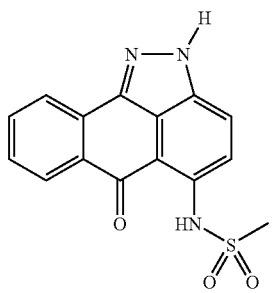

This compound may be made in the same manner using methanesulfonyl chloride as the sulfonyl chloride.

G. 5-(3-Benzenesulfonylamino)anthra[1,9cd]pyrazol-6(2H)-one

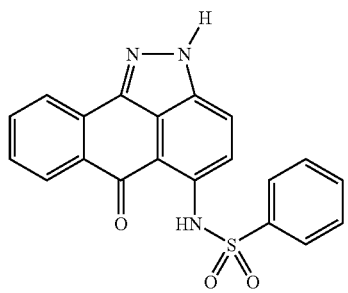

This compound may be made in the same manner using benzenesulfonyl chloride as the sulfonyl chloride.

Example 5

Synthesis of Representative Compounds

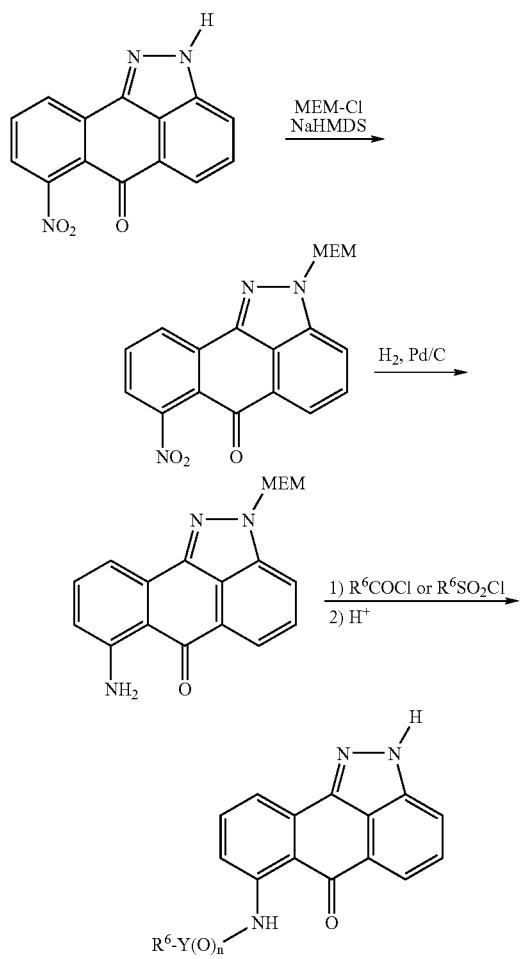

Y = C, n = 1
Y = S, n = 2

A. 7-(Benzoylamino)anthra[1,9cd]pyrazol-6(2H)-one

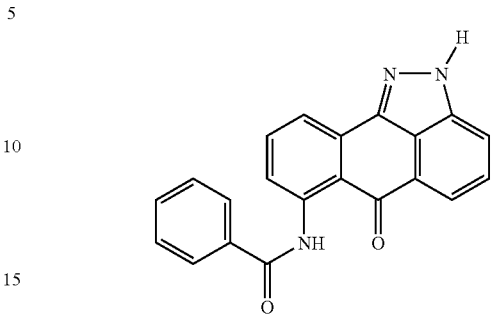

Benzoyl chloride is added to a solution of 2-(methoxyethoxymethyl)-7-aminoanthra[1,9cd]pyrazol-6-(2H)one and triethylamine in methylene chloride at 0° C. The mixture is stirred for 16 hours, quenched with water, and extracted with ethyl acetate (×2). The combined organic layer is washed with sodium bicarbonate solution, and brine, dried and evaporated. The crude reaction mixture is then taken in aqueous 6N hydrochloric acid, and heated at 80° C. for 4 hours. After cooling, the mixture is extracted with ethyl acetate (×2), washed with brine, dried, and evaporated. The reside is chromatographed on silica gel to furnish the desired amide as a yellow solid.

The starting material is prepared as follows. Sodium hexamethyldisilazide is added to a cooled (0° C.) solution of 7-nitroanthra[1,9cd]pyrazol-6(2H)-one (Example 1-E) in tetrahydrofuran, and the mixture is stirred for 30 minutes at 0° C. MEM-chloride is added, and the mixture is stirred for 16 hours at room temperature. Water is added and the mixture is extracted with ethyl acetate (×2). The combined organic layer is washed with aqueous sodium bicarbonate solution, water, 1N hydrochloric acid, and brine, dried and evaporated. The residue is chromatographed on silica gel to give 2-MEM-7-nitroanthra[1,9cd]pyrazol-6(2H)-one as an oil.

Palladium(10%) on charcoal and 2-MEM-5-nitroanthra[1,9cd]pyrazol-6(2H)-one in ethanol is placed under 1-atm of hydrogen, and the mixture was stirred for 6 hours. The catalyst is filtered off over celite, and the filtrate is evaporated to dryness to give 2-(methoxyethoxymethyl)-7-aminoanthra[1,9cd]pyrazol-6-(2H)one, which is used without further purification.

B. 7-(Isonicotinylamino)anthra[1,9cd]pyrazol-6(2H)-one

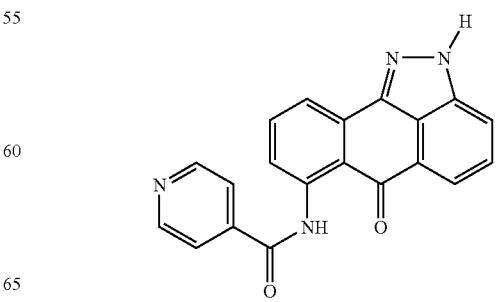

This compound may be made in the same manner using isonicotinoyl chloride as the acid chloride.

C. 7-(Nicotinylamino)anthra[1,9cd]pyrazol-6(2H)-one

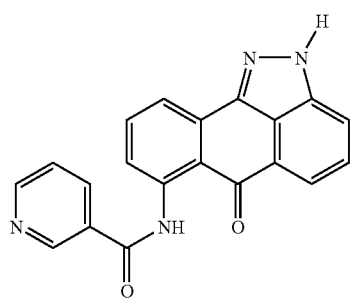

This compound may be made in the same manner using nicotinoyl chloride as the acid chloride.

D. 5-(2-Thiophenecarbonylamino)anthra[1,9cd]pyrazol-6(2H)-one

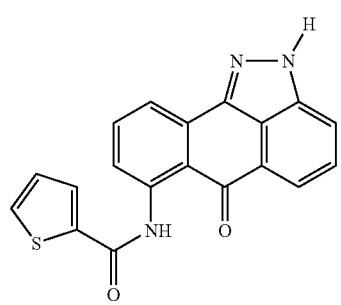

This compound may be made in the same manner using 2-thiophenecarboxylic acid chloride as the acid chloride.

E. 7-(3-Methylbutyrylamino)anthra[1,9cd]pyrazol-6(2H)-one

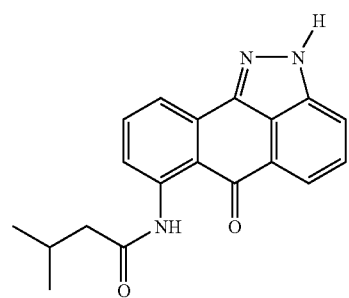

This compound may be made in the same manner using isopentanoyl chloride as the acid chloride.

F. 7-(3-Methanesulfonylamino)anthra[1,9cd]pyrazol-6(2H)-one

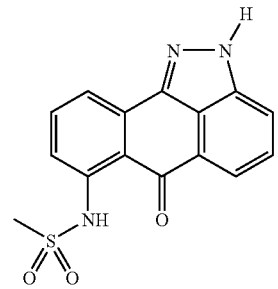

This compound may be made in the same manner using methanesulfonyl chloride as the sulfonyl chloride.

G. 7-(3-Benzenesulfonylamino)anthra[1,9cd]pyrazol-6(2H)-one

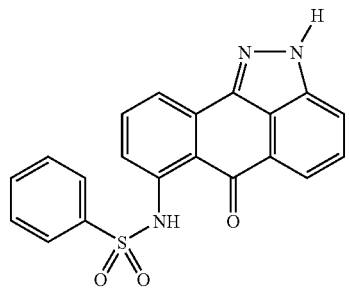

This compound may be made in the same manner using benzenesulfonyl chloride as the sulfonyl chloride.

Example 6

Synthesis of Representative Compounds

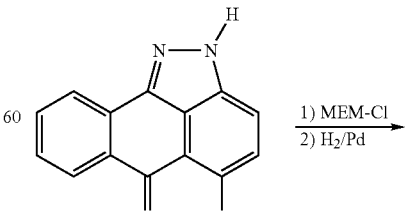

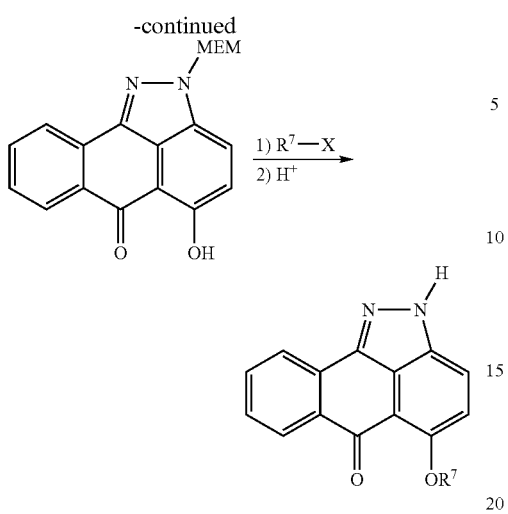

A.
5-(3-Methylbutyloxy)anthra[1,9cd]prazol-6(2H)-one

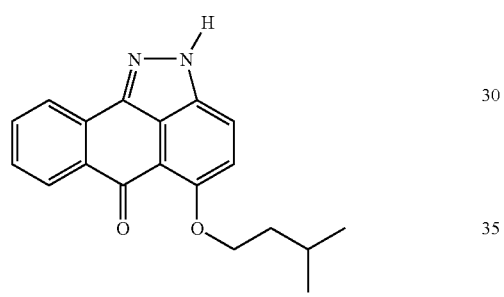

Isopentyl bromide is added to a mixture of 3-(2-methoxyethoxymethyl)5-hydroxyanthra[1,9cd]pyrazol-6(2H)-one and potassium carbonate in dimethylformamide at room temperature. After stirring the mixture for sixteen hours, water is added, and the mixture was extracted with ethyl acetate (×2). The combined organic layer is washed with aqueous sodium bicarbonate, water, 1N hydrochloric acid, and brine, dried and evaporated. The reside is taken in 6N hydrochloric acid and heated at 80° C. for 4 hours. After cooling, the mixture is extracted with ethyl acetate (×2), and the combined organic layer is washed with brine, dried, and evaporated. The residue is purified by column chromatography to afford the title compound as yellow solid.

The starting material is prepared as follows. Sodium hexamethyldisilazide is added to a cooled (0° C.) solution of 5-benzyloxyanthra[1,9cd]pyrazol-6(2H)-one (Example 1-F) in tetrahydrofuran, and the mixture is stirred for 30 minutes at 0° C. MEM-chloride is added, and the mixture is stirred for 16 hours at room temperature. Water is added and the mixture is extracted with ethyl acetate (×2). The combined organic layer is washed with aqueous sodium bicarbonate solution, water, 1N hydrochloric acid, and brine, dried and evaporated. The residue is chromatographed on silica gel to give 2-MEM-5-benzyloxyanthra[1,9cd]pyrazol-6(2H)-one as an oil.

Palladium(10%) on charcoal and 2-MEM-5-benzyloxyanthra[1,9cd]pyrazol-6(2H)-one in ethanol is placed under 1-atm of hydrogen, and the mixture stirred for 6 hours. The catalyst is filtered off over celite, and the filtrate is evaporated to dryness to give 2-(2-methoxyethoxymethyl)-5-hydroxyanthra[1,9cd]pyrazol-6-(2H)one, which is used without further purification.

B.
5-(4-Pyridylmethoxy)anthra[1,9cd]pyrazol-6(2H)-one

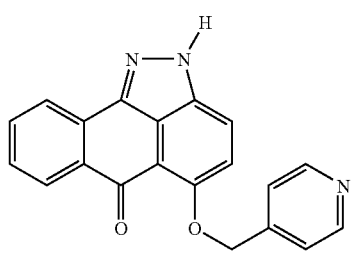

This compound may be made in the same manner using chloromethyl-4-pyridine as the alkyl halide.

C.
5-(3-Pyridylmethoxy)anthra[1,9cd]pyrazol-6(2H)-one

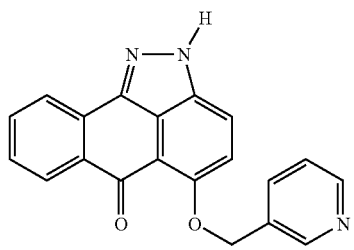

This compound may be made in the same manner using chloromethyl-3-pyridine as the alkyl halide.

D.
5-(2-Methoxyethoxy)anthra[1,9cd]pyrazol-6(2H)-one

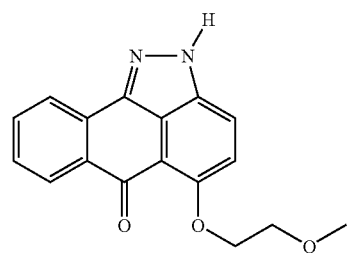

This compound may be made in the same manner using 2-methoxyethyl bromide as the alkyl halide.

E. 5-(2-Dimethylaminoethoxy)anthra[1,9cd]pyrazol-6(2H)-one

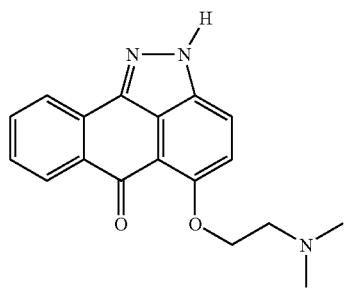

This compound may be made in the same manner using 2-dimethylaminoethyl chloride as the alkyl halide.

Example 7

Synthesis of Representative Compounds

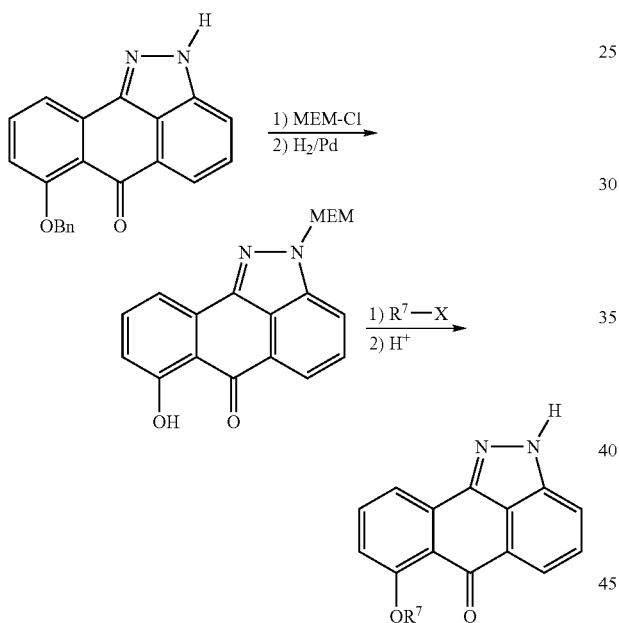

A.
7-(3-Methylbutyloxy)anthra[1,9cd]pyrazol-6(2H)-one

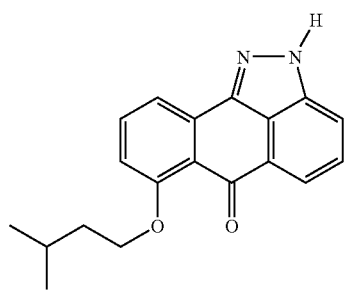

Isopentyl bromide is added to a mixture of 3-(2-methoxyethoxymethyl)-7-hydroxyanthra[1,9cd]pyrazol-6(2H)-one and potassium carbonate in dimethylformamide at room temperature. After stirring the mixture for sixteen hours, water is added, and the mixture was extracted with ethyl acetate (×2). The combined organic layer is washed with aqueous sodium bicarbonate, water, 1N hydrochloric acid, and brine, dried and evaporated. The reside is taken in 6N hydrochloric acid and heated at 80° C. for 4 hours. After cooling, the mixture is extracted with ethyl acetate (×2), and the combined organic layer is washed with brine, dried, and evaporated. The residue is purified by column chromatography to afford the title compound as yellow solid.

The starting material is prepared as follows. Sodium hexamethyldisilazide is added to a cooled (0° C.) solution of 7-benzyloxyanthra[1,9cd]pyrazol-6(2H)-one (Example 1-F) in tetrahydrofuran, and the mixture is stirred for 30 minutes at 0° C. MEM-chloride is added, and the mixture is stirred for 16 hours at room temperature. Water is added and the mixture is extracted with ethyl acetate (×2). The combined organic layer is washed with aqueous sodium bicarbonate solution, water, 1N hydrochloric acid, and brine, dried and evaporated. The residue is chromatographed on silica gel to give 2-MEM-7-benzyloxyanthra[1,9cd]pyrazol-6(2H)-one as an oil.

Palladium(10%) on charcoal and 2-MEM-7-benzyloxyanthra[1,9cd]pyrazol-6(2H)-one in ethanol is placed under 1-atm of hydrogen, and the mixture was stirred for 6 h. The catalyst is filtered off over celite, and the filtrate is evaporated to dryness to give 2-(2-methoxyethoxymethyl)-7-hydroxyanthra[1,9cd]pyrazol-6-(2H)one, which is used without further purification.

B.
7-(4-Pyridylmethoxy)anthra[1,9cd]pyrazol-6(2H)-one

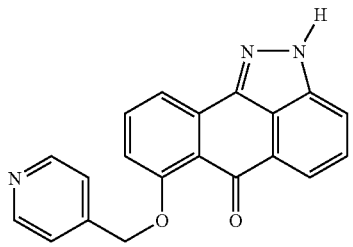

This compound may be made in the same manner using chloromethyl-4-pyridine as the alkyl halide.

C.
7-(3-Pyridylmethoxy)anthra[1,9cd]pyrazol-6(2H)-one

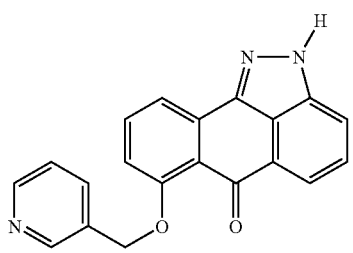

This compound may be made in the same manner using chloromethyl-3-pyridine as the alkyl halide.

D.
7-(2-Methoxyethoxy)anthra[1,9cd]pyrazol-6(2H)-one

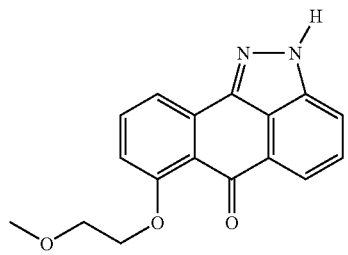

This compound may be made in the same manner using 2-methoxyethyl bromide as the alkyl halide.

E. 7-(2-Dimethylaminoethoxy)anthra[1,9cd]pyrazol-6(2H)-one

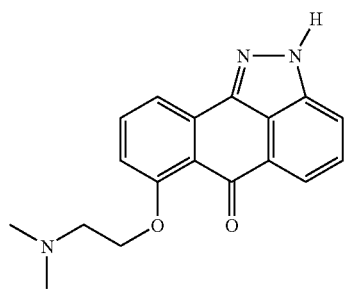

This compound may be made in the same manner using 2-dimethylaminoethyl chloride as the alkyl halide.

Example 8

Activity of Representative Compound

The compounds of this invention may be assayed for their activity accordingly to the following procedures.

JNK Assay

To 10 μL of the test compound in 20% DMSO/80% dilution buffer consisting of 20 mM HEPES (pH 7.6), 0.1 mM EDTA, 2.5 mM magnesium chloride, 0.004% Triton ×100, 2 μg/mL leupeptin, 20 mM β-glycerolphosphate, 0.1 mM sodium vanadate, and 2 mM DTT in water is added 30 μL of 50–200 ng His6-JNK1, JNK2 or JNK3 in the same dilution buffer. The mixture is preincubated for 30 minutes at room temperature. Sixty microliter of 10 μg GST-c-Jun (1-79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton ×100, 11 μM ATP, and 0.5 μCi γ-32P ATP in water is added and the reaction is allowed to proceed for 1 hour at room temperature. The c-Jun phosphorylation is terminated by addition of 150 μL of 12.5% trichloroacetic acid. After 30 minutes, the precipitate is harvested onto a filter plate, diluted with 50 μL of the scintillation fluid and quantified by a counter. The $IC_{50}$ values are calculated as the concentration of the test compound at which the c-Jun phosphorylation is reduced to 50% of the control value. Preferred compounds of the present invention have an $IC_{50}$ value ranging 0.01–10 μM in this assay. To this end, a preferred compound of this invention is Compound 1, which has an $IC_{50}$ according to this assay of 0.11 μM for JNK1 and JNK2, and 0.15 μM for JNK3.

Selectivity for JNK

Figure 2:
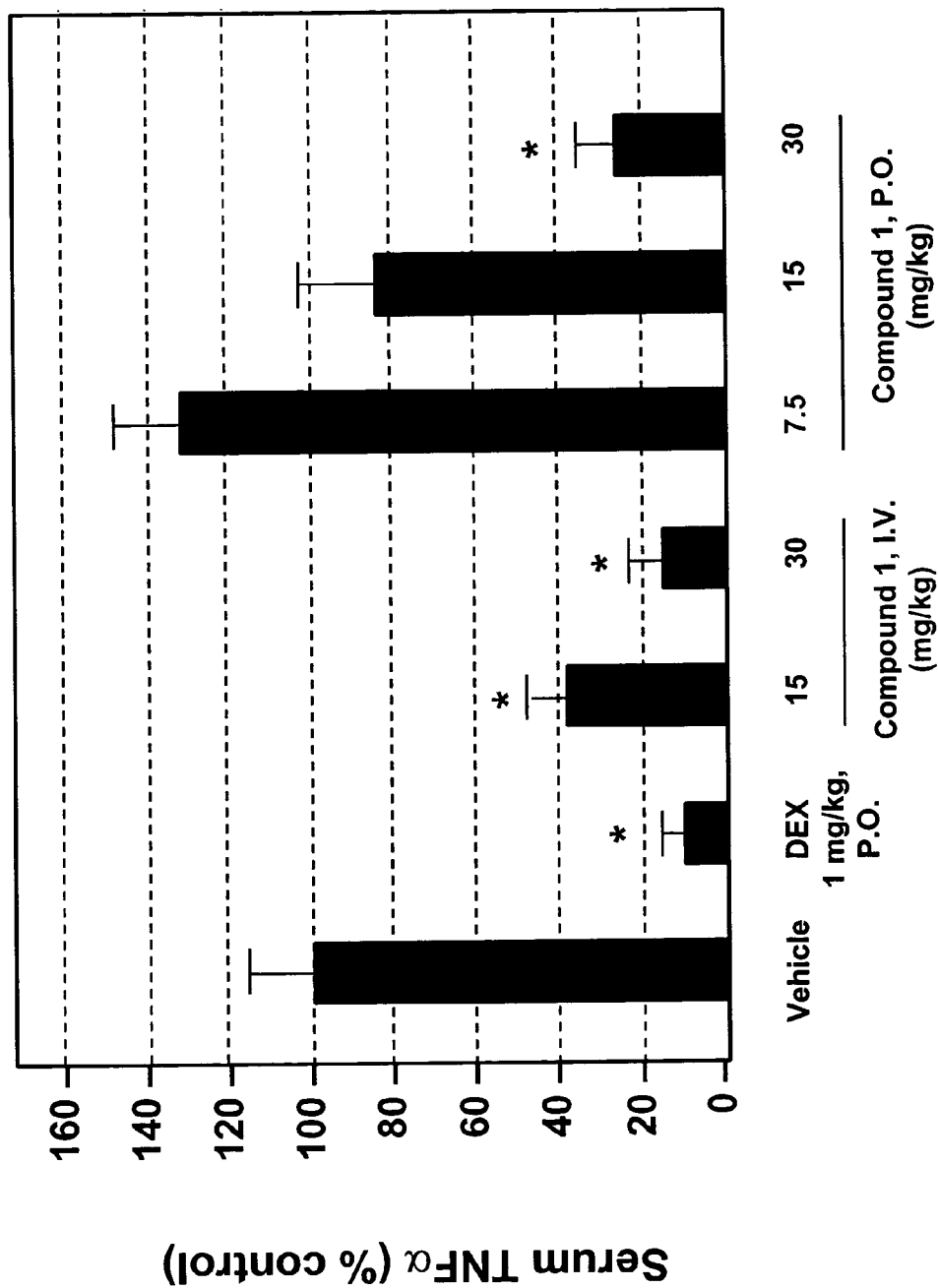
FIG. 2 illustrates the ability of a representative compound of this invention to inhibit TNF-α in a mouse model of endotoxin shock.

Compound 1 was also assayed for its inhibitory activity against the following protein kinases by techniques known to those skilled in this field (see, e.g., *Protein Phosphorylation*, Sefton & Hunter, Eds., Academic Press, pp. 97–367, 1998):

Enzyme $IC_{50}$
p38-2 >30,000 nM
ERK1 >30,000 nM
MEKK1 >30,000 nM
IKK1 >30,000 nM
IKK2 >30,000 nM
PKA >30,000 nM
PKC >10,000 nM
EGF-TK >10,000 nM Jurkat T-cell Il-2 Production Assay Jurkat T cells (clone E6-1) are purchased from the American Tissue Culture Collection and maintained in growth media consisting of RPMI 1640 medium containing 2 mM L-glutamine (Mediatech), with 10% fetal bovine serum (Hyclone) and penicillin/streptomycin. All cells are cultured at 37° C. in 95% air and 5% $CO_2$. Cells are plated at a density of $0.2 \times 10^6$ cells per well in 200 μL of media. Compound stock (20 mM) is diluted in growth media and added to each well as a 10× concentrated solution in a volume of 25 μL, mixed, and allowed to pre-incubate with cells for 30 minutes. The compound vehicle (dimethylsulfoxide) is maintained at a final concentration of 0.5% in all samples. After 30 minutes the cells are activated with PMA (phorbol myristate acetate; final concentration 50 ng/mL) and PHA (phytohemagglutinin; final concentration 2 μg/mL). PMA and PHA are added as a 10× concentrated solution made up in growth media and added in a volume of 25 μL per well. Cell plates are cultured for 10 hours. Cells are pelleted by centrifugation and the media removed and stored at −20° C. Media aliquots are analyzed by sandwich ELISA for the presence of IL-2 as per the manufacturers instructions (Endogen). The $IC_{50}$ values are calculated as the concentration of the test compound at which the Il-2 production was reduced to 50% of the control value. Preferred compounds of the present invention have an $IC_{50}$ value ranging 0.1—30 μM in this assay. FIG. 1 presents the dose dependent inhibition of IL-2 in Jarkat T-Cells by Compound 1 according to this procedure, with a resulting $IC_{50}$ of 5 μM Mouse In Vivo LPS-Induced TNF-α Production Assay Non-fasted mice are acclimatized for at least 7 days. Groups of 4 to 6 female BALB/c or CD-1 mice (8–10 weeks of age from Charles River laboratories) are pretreated with test compound, either by intravenous injection or by oral gavage 15–180 minutes prior to the injection of 0.5 mg/kg Bacto LPS from *E. coli* 055:B5 (Difco Labs). Ninety minutes after LPS challenge, a terminal bleed is performed via abdominal vena cava and blood is allowed to clot at room temperature for 30 minutes in Microtainer serum separator tubes. After separation by centrifugation, the serum is stored frozen at —80° C. ELIZA is performed on thawed, diluted samples (1:10 to 1:20) using a Mouse TNF-alpha kit (Biosource International). The $ED_{50}$ values are calculated as the dose of the test compound at which the TNF-α production is reduced to 50% of the control value. Preferred compounds of the present invention have an $ED_{50}$ value ranging 1–30 mg/kg in this assay. FIG. 2 illustrates the results of this experiment utilizing Compound 1 administered by intravenous injection (I.V.) at 15 and 30 mg/kg, as well as by per os (P.O.) at 7.5, 15 and 30 mg/kg. Vehicle alone (PEG-400, propylene glycol, cremophor EL, and ethanol in normal saline, "PPCES") and dexamethasone-21 acetate ("DEX") (1 mg/kg P.O.) were run as controls (n=6, *=p 0.01). Compound 1 was administered 15 minutes pre-LPS challenge, and bleed occurred 90 minutes post LPS.

Inhibition of Leukocyte Recruitment in Rat Inflamed Lung

Figure 3:
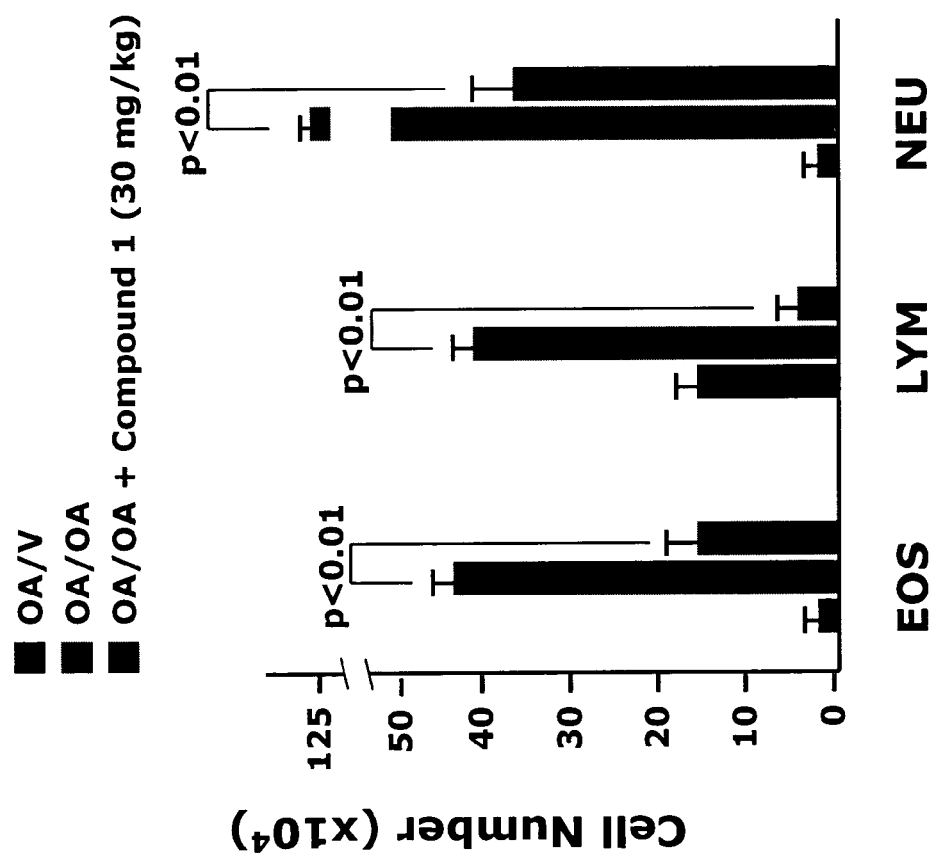
FIG. 3 illustrates the ability of a representative compound of this invention to inhibit leukocyte recruitment in rat model for inflamed lung.

Aerosol administration of ovalbumun in Brown Norway Rats previously sensitized by injection of ovalbumin (OA) results in an allergic airway inflammation marked by the generation of an eosinophil- and T-lymphocyte-rich leukocytic infiltration in the lungs (see Richards et al., *Am. J. Physiol*, 271:2 Pt 1, L267–76, 1996). Compound 1 was administered by subcutaneous injection at a dose of 30 mg/kg, b.i.d. for 3 days prior to ovalbumin challenge by aerosol. Cells counts were obtained from samples of broncho-alveolar lavage, the results of which are illustrated in FIG. 3 (V=PPCES vehicle).

Rat In Vivo Adjuvant Arthritis

Figure 4A:
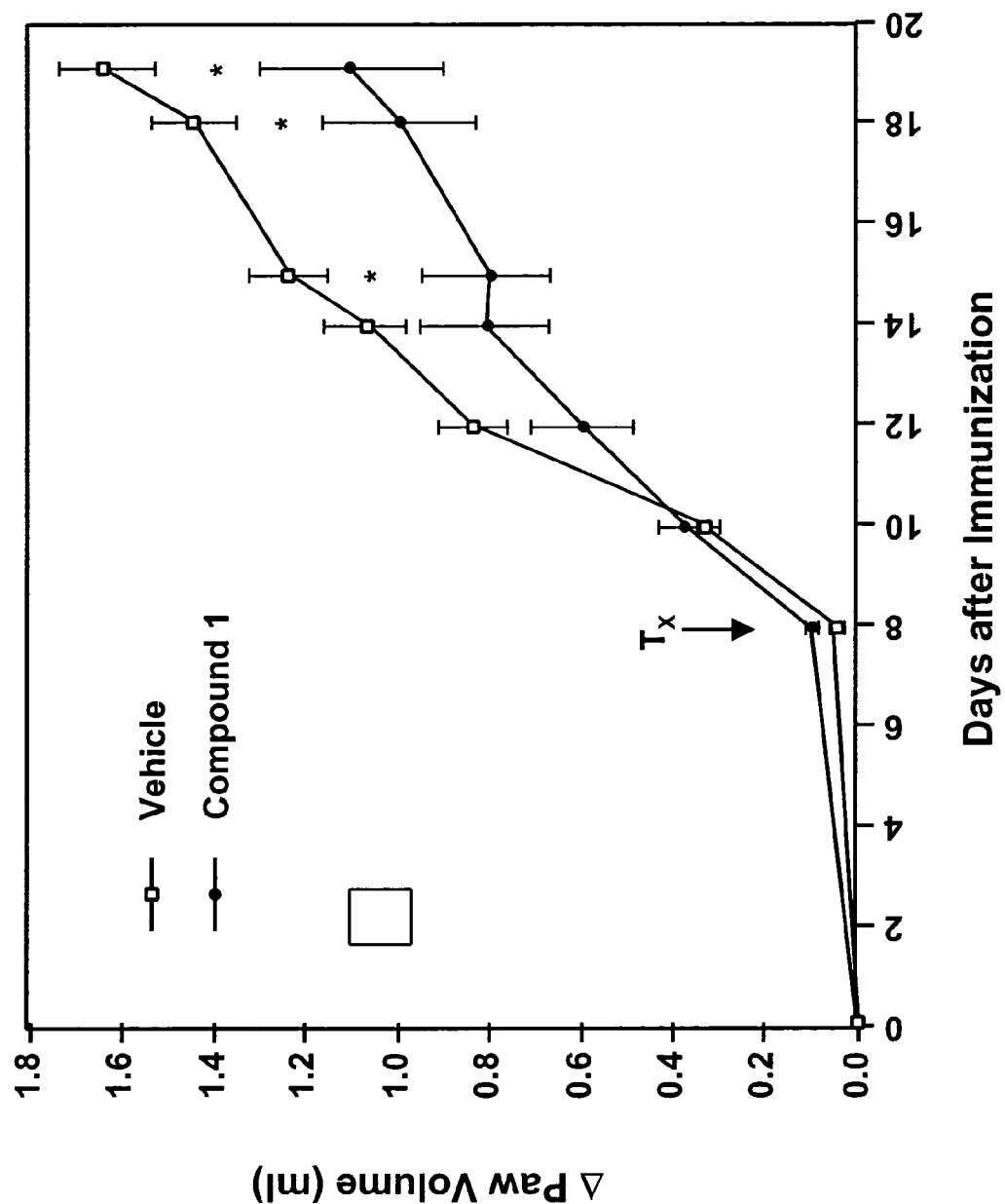
FIG. 4 illustrates the ability of a representative compound of this invention to inhibit paw swelling (FIG. 4A), joint destruction (FIG. 4B), transcription factor AP-1 activation (FIG. 4C), and expression of MMP-13 (FIG. 4D) in a rat model for adjuvant arthritis.
Figure 4B:
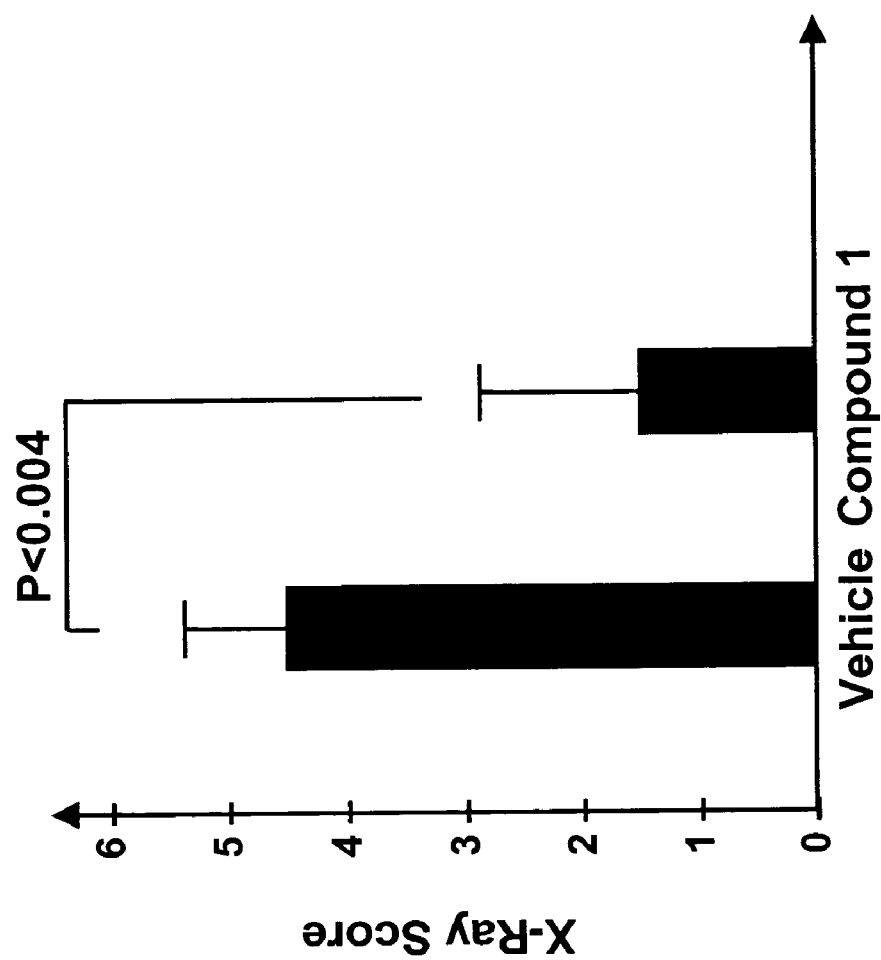
Figure 4C:
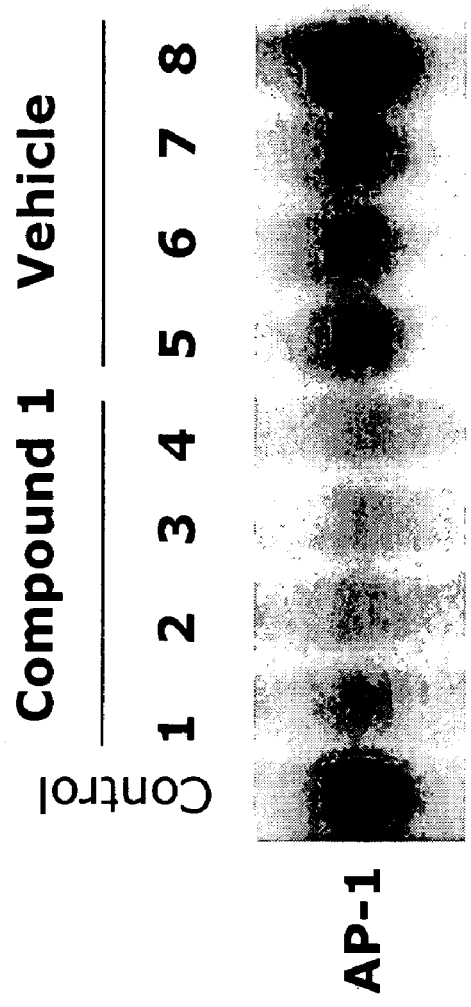
Figure 4D:
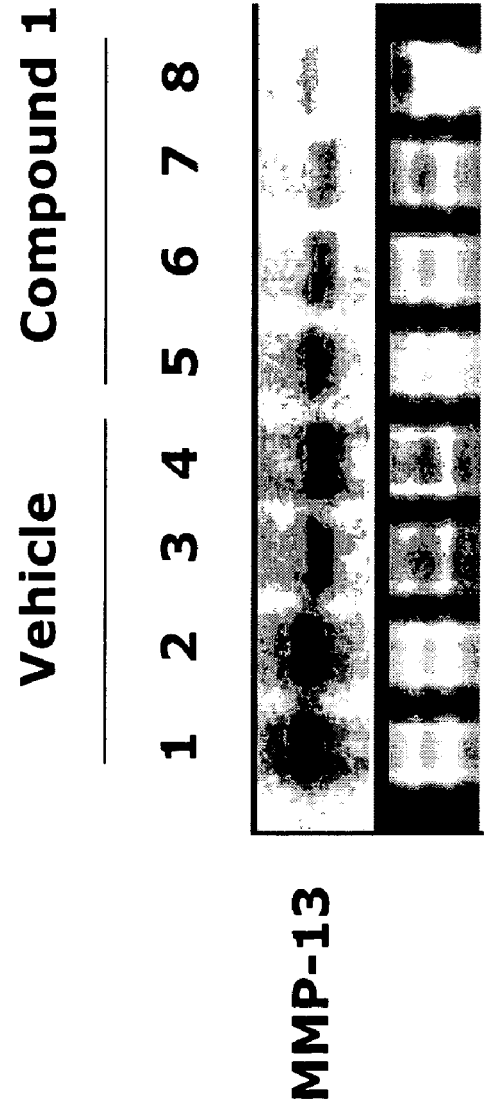

Male Lewis rats were immunized with complete Freund's adjuvant on day 0 to induce an aggressive arthritis characterized by joint destruction and paw swelling. Compound 1 was administered subcutaneously once daily from day 8 to day 20. Paw swelling was determined be water displacement plethysmometry (see FIG. 4A; *=p<0.01). Radiographs were obtained of the right hind paw to assess bone changes using a semi-quantitative scoring system: demineralization (0-2+), calcaneal erosion (0-1+), and heterotropic bone formation (0-1+), with a maximum possible score 6 (see FIG. 4B). Activation of AP-1 (see FIG. 4C) was determined by DNA binding activity in an electrophoretic mobility shift assay (EMSA) (Ausubel et al., *Short Protocols in Molecular Biology*, Second Edition, John Wiley & Sons Publisher, New York, 1992). Matrix metalloproteinase-13 expression (see FIG. 4D) was measured by nothern blot analysis of MMP-13 mRNA (Ausebel et al., supra) (see also Winter et al., *Arthritis and Rheumatism* 9(3):394–404, 1966; Weichman et al., *Pharmacological Methods in the Control of Inflammation*, Chang and Lewis Eds., Alan R. Liss, Inc., Publ., New York, 1989).

Kainic Acid-Induced Seizure Response

Figure 5:
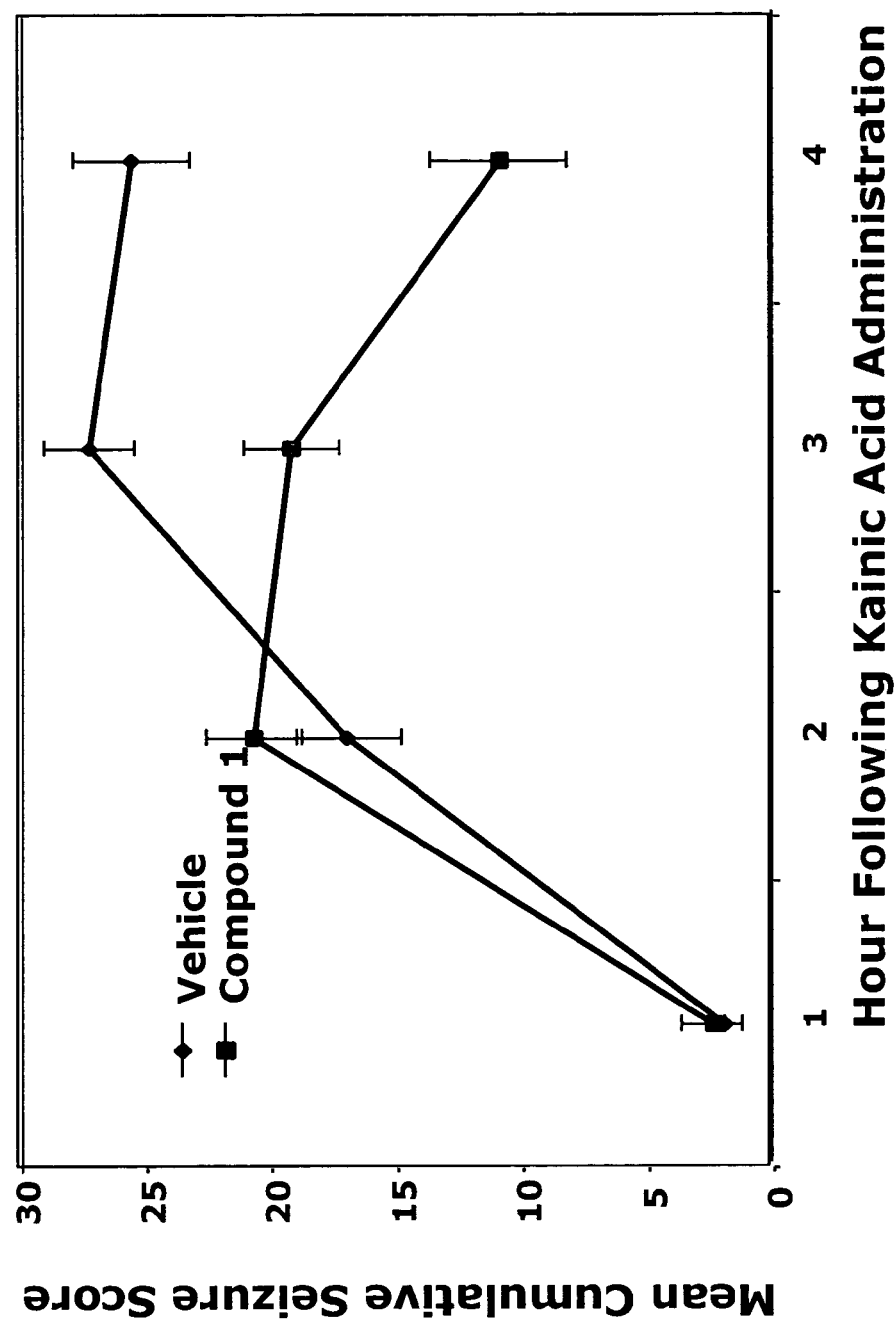
FIG. 5 illustrates the ability of a representative compound of this invention to reduce kainic acid-induced seizure response.

Compound 1 was administered to male CD rats at 10 mg/kg intravenously through a tail vein catheter. This was followed immediately by a 30 mg/kg subcutaneous injection. Vehicle controls received the same injection volumes of the PPCES vehicle alone. Thirty minutes later, animals were given a 1-mg/kg i.p. injection of kainic acid in normal saline solution. This dose of kainic acid has been previously reported to induce a seizure syndrome in rats (Maj et al., *Eur. J. Pharm.* 359:27–32, 1992). Seizure behavior was monitored for 4 hours following kainic acid injection. As presented in FIG. 5, behaviors were assessed based on the following cumulative scoring system: 1 pt.=arrest of motion; 2 pts.=myoclonic jerks of the head and neck (moderate); 3 pts.=unilateral or bilateral forelimb clonic activity; 4 pts.=whole body clonus; 5 pts.=clonic-tonic seizures; 6 pts.=status epilepticus (see also Mathis and Ungerer, *Exp. Brain Res.* 88:277–282, 1992; Rong et al., *Proc. Natl. Acad. Sci. USA* 96:9897–9902, 1999; Yang et al., *Nature* 389: 865–870, 1997)

It will be appreciated that, although specific embodiments of the invention have been described herein for purposes of illustration, various modifications may be made without departing from the spirit and scope of the invention. Accordingly, the invention is not limited except as by the appended claims.

The invention claimed is:

1. A compound having the structure:

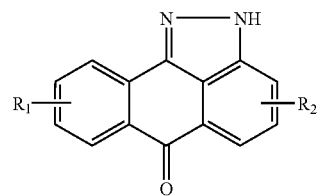

or a pharmaceutically acceptable salt thereof, wherein $R_1$ and $R_2$ are optional substituents that are the same or different and independently represent trifluoromethyl, sulfonyl, aryl, arylalkyloxy, arylalkyl, cycloalkylalkyloxy, cycloalkyloxy, alkoxyalkoxy, aminoalkoxy, mono- or di-alkylaminoalkoxy, or a group represented by formula (a), (b), (c) or (d):

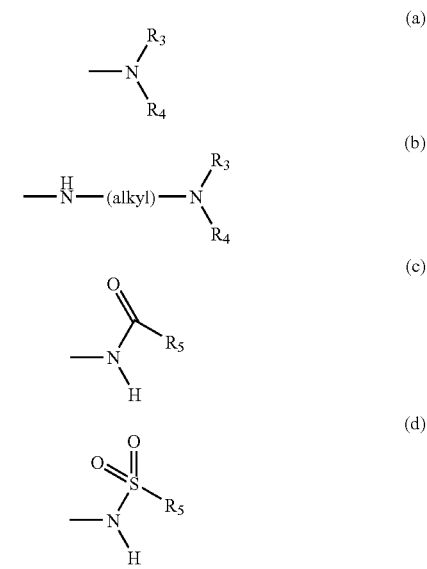

$R_3$ and $R_4$ are the same or different and independently represent cycloalkyl, aryl, arylalkyl, cycloalkylalkyl, aryloxyalkyl, alkoxyalkyl, alkoxyamino, or alkoxy (mono- or di-alkylamino); and $R_5$ represents hydrogen, alkyl, cycloalkyl, carbocyclic aromatic, heterocyclic aromatic, arylalkyl, cycloalkylalkyl, alkoxy, amino, mono- or di-alkylamino, arylamino, arylalkylamino, cycloalkylamino or cycloalkylalkylamino, with the proviso that carbocyclic aromatic is not phenyl;

and with the proviso that at least $R_1$ or $R_2$ is present.

2. A compound having one of the following structures:

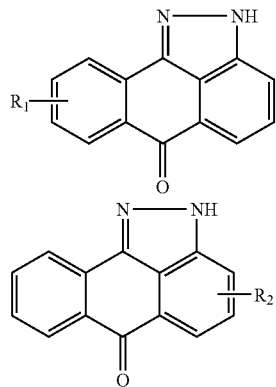

or a pharmaceutically acceptable salt thereof,
wherein
R₁ represents trifluoromethyl, sulfonyl, carboxyl, alkoxycarbonyl, aryl, arylalkyloxy, arylalkyl, cycloalkylalkyloxy, cycloalkyloxy, alkoxyalkoxy, aminoalkoxy, mono- or di-alkylaminoalkoxy, or a group represented by formula (a), (b), (c) or (d):

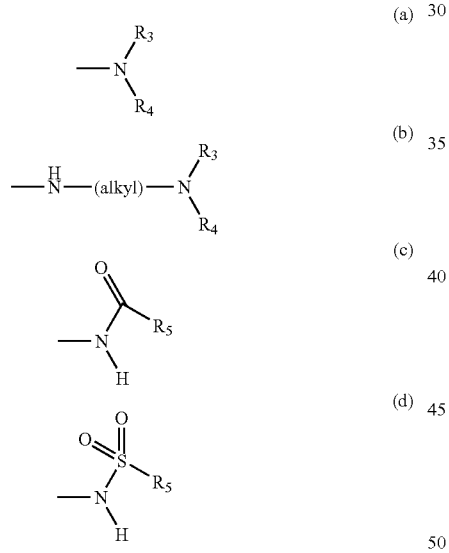

when R₁ is present, R₃ and R₄ are the same or different and independently represent alkyl, cycloalkyl, aryl, arylalkyl, cycloalkylalkyl, aryloxyalkyl, alkoxyalkyl, alkoxyamino, or alkoxy(mono- or di-alkylamino);

when R₁ is present, R₅ represents hydrogen, alkyl, cycloalkyl, aryl, arylalkyl, cycloalkylalkyl, alkoxy, amino, mono- or di-alkylamino, arylamino, arylalkylamino, cycloalkylamino or cycloalkylalkylamino;

R₂ represents trifluoromethyl, sulfonyl, aryl, arylalkyloxy, arylalkyl, cycloalkylalkyloxy, cycloalkyloxy, alkoxyalkyl, alkoxyalkoxy, aminoalkoxy, mono- or di-alkylaminoalkoxy, or a group represented by formula (a), (b), (c) or (d):

(a)

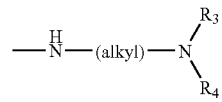
(b)

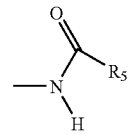
(c)

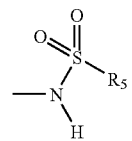
(d)

when R₂ is present, R₃ and R₄ are the same or different and independently represent cycloalkyl, aryl, arylalkyl, cycloalkylalkyl, aryloxyalkyl, alkoxyalkyl, alkoxyamino, or alkoxy(mono- or di-alkylamino); and when R₂ is present, R₅ represents hydrogen, alkyl, cycloalkyl, carbocyclic aromatic, heterocyclic aromatic, arylalkyl, cycloalkylalkyl, alkoxy, amino, mono- or di-alkylamino, arylamino, arylalkylamino, cycloalkylamino or cycloalkylalkylamino with the proviso that carbocyclic aromatic is not phenyl.

3. The compound of claim 2 wherein R₁ and R₂ are:

4. The compound of claim 2 wherein R₁ and R₂ are:

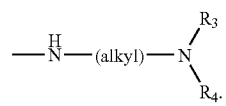

5. The compound of claim 2 wherein R₁ and R₂ are:

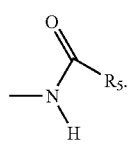

6. The compound of claim 2 wherein $R_1$ and $R_2$ are:

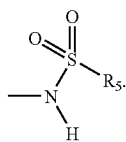

7. A composition comprising the compound or pharmaceutically acceptable salt of the compound of claim 1 and a pharmaceutically acceptable carrier or a pharmaceutically acceptable diluent.

8. A pharmaceutical composition comprising a compound having the structure:

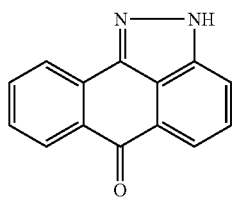

or a pharmaceutically acceptable salt thereof, a pharmaceutically acceptable carrier or a pharmaceutically acceptable diluent and a dispersing agent, a surface active agent, a binder or a lubricant.

9. A compound having the structure:

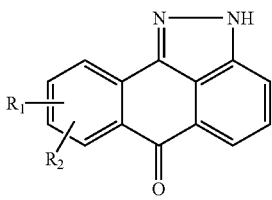

or a pharmaceutically acceptable salt thereof,
wherein
$R_1$ and $R_2$ are optional substituents that are the same or different and independently represent, trifluoromethyl, sulfonyl, carboxyl, alkoxycarbonyl, aryl, arylalkyloxy, arylalkyl, cycloalkylalkyloxy, cycloalkyloxy, alkoxyalkyl, alkoxyalkoxy, aminoalkoxy, mono- or di-alkylaminoalkoxy, or a group represented by formula (a), (b), (c) or (d):

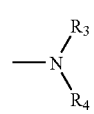 (a)

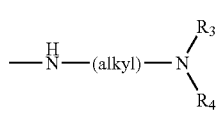 (b)

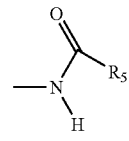 (c)

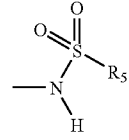 (d)

$R_3$ and $R_4$ are the same or different and independently represent alkyl, cycloalkyl, aryl, arylalkyl, cycloalkylalkyl, aryloxyalkyl, alkoxyalkyl, alkoxyamino, or alkoxy(mono- or di-alkylamino); and $R_5$ represents hydrogen, alkyl, cycloalkyl, aryl, arylalkyl, cycloalkylalkyl, alkoxy, amino, mono- or di-alkylamino, arylamino, arylalkylamino, cycloalkylamino or cycloalkylalkylamino;

and with the proviso that at least one of $R_1$ or $R_2$ is present.

10. The composition of claim 7, wherein the composition is a pharmaceutical composition.

11. The composition of claim 7, wherein the compound or pharmaceutically acceptable salt of the compound is present in an amount that is effective for inhibiting JNK.

12. The composition of claim 10, wherein the composition is in the form of a pill, tablet or capsule.

13. The composition of claim 8 or 10, wherein the composition is suitable for oral administration.

14. The composition of claim 8 or 10, wherein the composition is suitable for parenteral administration.

15. The composition of claim 8 or 10, wherein the compound is present in an amount from 0.1 mg to 250 mg per dosage.

16. The composition of claim 8 or 10, wherein the compound is present in an amount from 1 mg to 60 mg per dosage.

17. A pharmaceutical composition comprising a compound or a pharmaceutically acceptable salt of the compound of claim 2 and a pharmaceutically acceptable carrier.

18. A pharmaceutical composition comprising a compound or a pharmaceutically acceptable salt of the compound of claim 9 and a pharmaceutically acceptable carrier.

19. A solid pharmaceutical composition selected from a pill, capsule or tablet, comprising a compound having the structure:

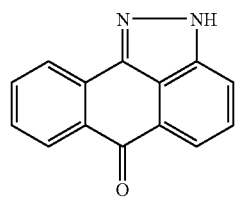

or a pharmaceutically acceptable salt thereof, and a pharmaceutically acceptable carrier or a pharmaceutically acceptable diluent.

* * * * *